(12) United States Patent
Siddiqui et al.

(10) Patent No.: US 9,421,317 B2
(45) Date of Patent: Aug. 23, 2016

(54) CELL HARVESTING DEVICE AND SYSTEM

(75) Inventors: Imran A. Siddiqui, Wantagh, NY (US); Gerard R. DelGiacco, Yonkers, NY (US); Paxton E. Provitera, East Meadow, NY (US)

(73) Assignee: Pall Corporation, Port Washington, NY (US)

(*) Notice: Subject to any disclaimer, the term of this patent is extended or adjusted under 35 U.S.C. 154(b) by 696 days.

(21) Appl. No.: 13/491,897

(22) Filed: Jun. 8, 2012

(65) Prior Publication Data

US 2013/0327722 A1    Dec. 12, 2013

(51) Int. Cl.
*A61M 1/36* (2006.01)
*A61M 5/165* (2006.01)
*A61M 1/34* (2006.01)

(52) U.S. Cl.
CPC ............ *A61M 1/3633* (2013.01); *A61M 1/3635* (2014.02); *A61M 5/165* (2013.01); *A61M 1/3496* (2013.01); *A61M 2202/0439* (2013.01)

(58) Field of Classification Search
CPC ............ A61M 1/3633; A61M 1/3635; A61M 1/3496; A61M 5/165; A61M 2005/1655; A61M 2202/005; A61M 2202/0413; A61M 2202/0439; B01D 29/0004; B01D 29/0027; B01D 29/0095; B01D 29/01; B01D 29/05; B01D 29/90; B01D 29/92; B01D 39/14; B01D 39/16; B01D 39/1607; B01D 2201/0407; B01D 2201/0415; G01N 30/6017; G01N 30/603

See application file for complete search history.

(56) References Cited

U.S. PATENT DOCUMENTS

| | | | |
|---|---|---|---|
| 3,202,286 A * | 8/1965 | Smit | B01D 24/266 210/286 |
| 3,374,606 A * | 3/1968 | Baddour | G01N 30/38 95/85 |
| 4,087,327 A | 5/1978 | Feder et al. | |
| 4,092,246 A | 5/1978 | Kummer | |
| 4,159,954 A | 7/1979 | Gangemi | |
| 4,375,415 A | 3/1983 | Lavender | |
| 4,382,808 A | 5/1983 | Van Wormer, Jr. et al. | |
| 4,450,082 A * | 5/1984 | Tanouchi | B01D 15/00 210/290 |
| 4,557,830 A * | 12/1985 | Onitsuka | B01D 15/22 210/198.2 |
| 4,880,548 A * | 11/1989 | Pall et al. | 210/767 |
| 4,923,620 A | 5/1990 | Pall | |
| 5,399,265 A | 3/1995 | Nehls | |
| 5,527,472 A | 6/1996 | Bellotti et al. | |
| 5,626,751 A | 5/1997 | Kikuchi et al. | |
| 5,690,825 A | 11/1997 | Parton | |
| 5,798,041 A * | 8/1998 | Zuk, Jr. | 210/456 |

(Continued)

FOREIGN PATENT DOCUMENTS

| | | |
|---|---|---|
| CN | 2436161 Y | 6/2001 |
| CN | 103484358 B | 8/2015 |

(Continued)

OTHER PUBLICATIONS

Notice of Reasons for Rejection, Japanese Application No. P2013-083946 dated Mar. 4, 2014.

(Continued)

*Primary Examiner* — David C Mellon
(74) *Attorney, Agent, or Firm* — Jeremy Jay

(57) ABSTRACT

Devices, methods, and systems for obtaining one or more biological fluid components, and reducing red blood cell contamination, using a back-flushable filter device, are disclosed.

19 Claims, 15 Drawing Sheets

(56) References Cited

U.S. PATENT DOCUMENTS

| | | |
|---|---|---|
| 6,268,119 B1 | 7/2001 | Sumita et al. |
| 6,544,751 B1 | 4/2003 | Brandwein et al. |
| 7,291,450 B2 | 11/2007 | Sowemimo-Coker et al. |
| 2005/0247627 A1 | 11/2005 | Bormann et al. |
| 2008/0081033 A1 | 4/2008 | Sowemimo-Coker et al. |
| 2010/0291629 A1 | 11/2010 | Fournier-Wirth et al. |
| 2011/0224645 A1 | 9/2011 | Winqvist et al. |
| 2012/0213754 A1 | 8/2012 | Chapman |
| 2013/0327712 A1 | 12/2013 | DelGiacco et al. |

FOREIGN PATENT DOCUMENTS

| | | |
|---|---|---|
| EP | 0 313 348 A2 | 4/1989 |
| JP | 57-145662 A | 9/1982 |
| JP | 2007-204016 A | 11/2007 |
| JP | 2007-304016 A | 11/2007 |
| JP | 2012-501708 A | 1/2012 |
| WO | WO 94/21124 A1 | 9/1994 |
| WO | WO 98/01207 | 1/1998 |
| WO | WO 2004/033396 A2 | 4/2004 |
| WO | WO 2005/052137 A1 | 6/2005 |
| WO | WO 2005/094914 A1 | 10/2005 |
| WO | WO 2008/005960 A2 | 1/2008 |
| WO | WO 2010/029317 A2 | 3/2010 |

OTHER PUBLICATIONS

European Search Report, European Application No. 13165135.8, dated Sep. 19, 2013.
Singapore Search Report, Singapore Application No. 201302774-3, dated Oct. 15, 2013.
Taiwan Application No. 102120090 Examination Report dated Dec. 19, 2014.
Sahin, B. et al. "The pressure distribution in and flow characteristics of wide-angle diffusers using perforated plates for flow control with application to electrostatic precipitators," *International Journal of Mechanical Sciences*, vol. 35(2), pp. 117-127 (1993).

\* cited by examiner

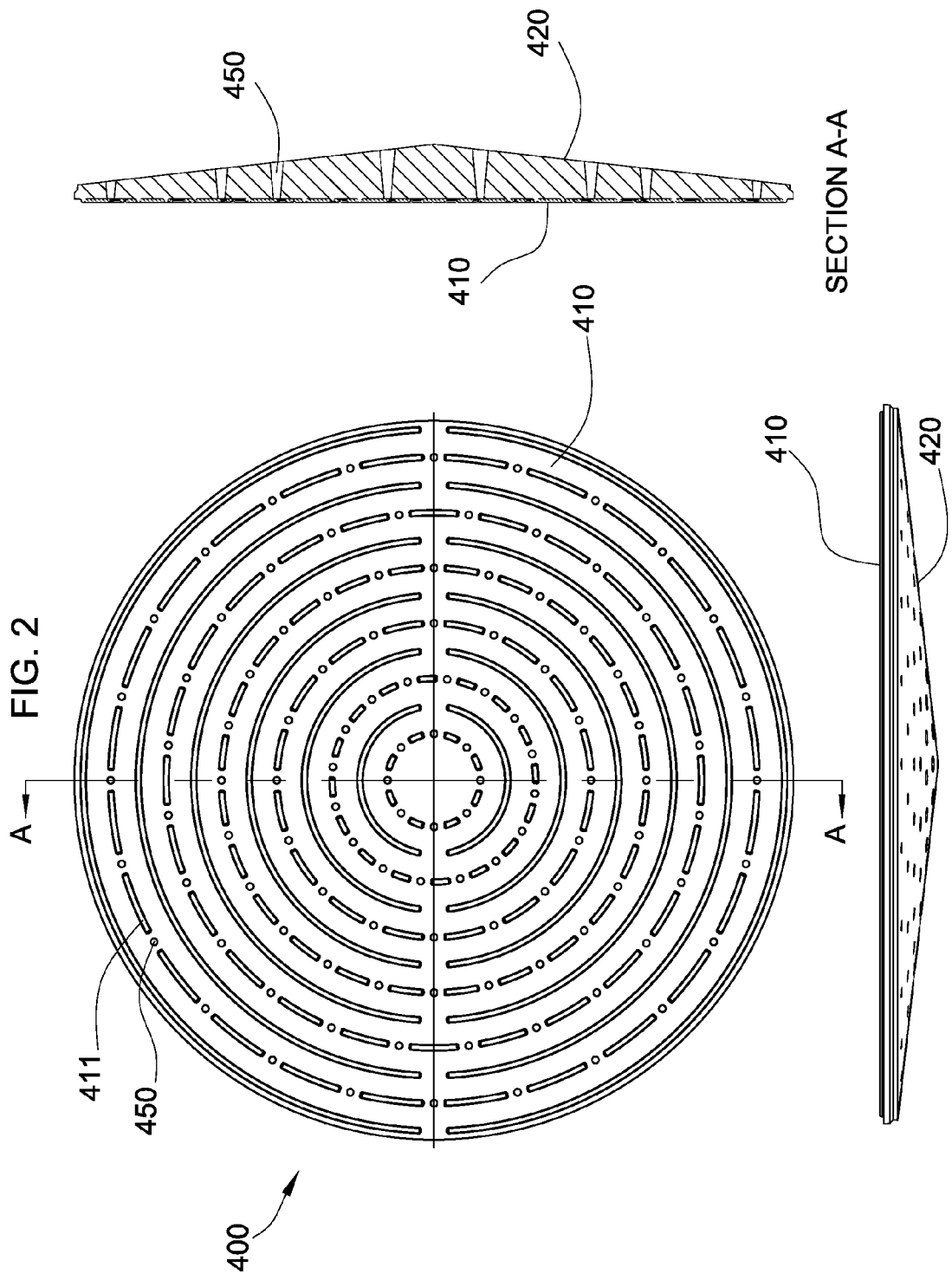

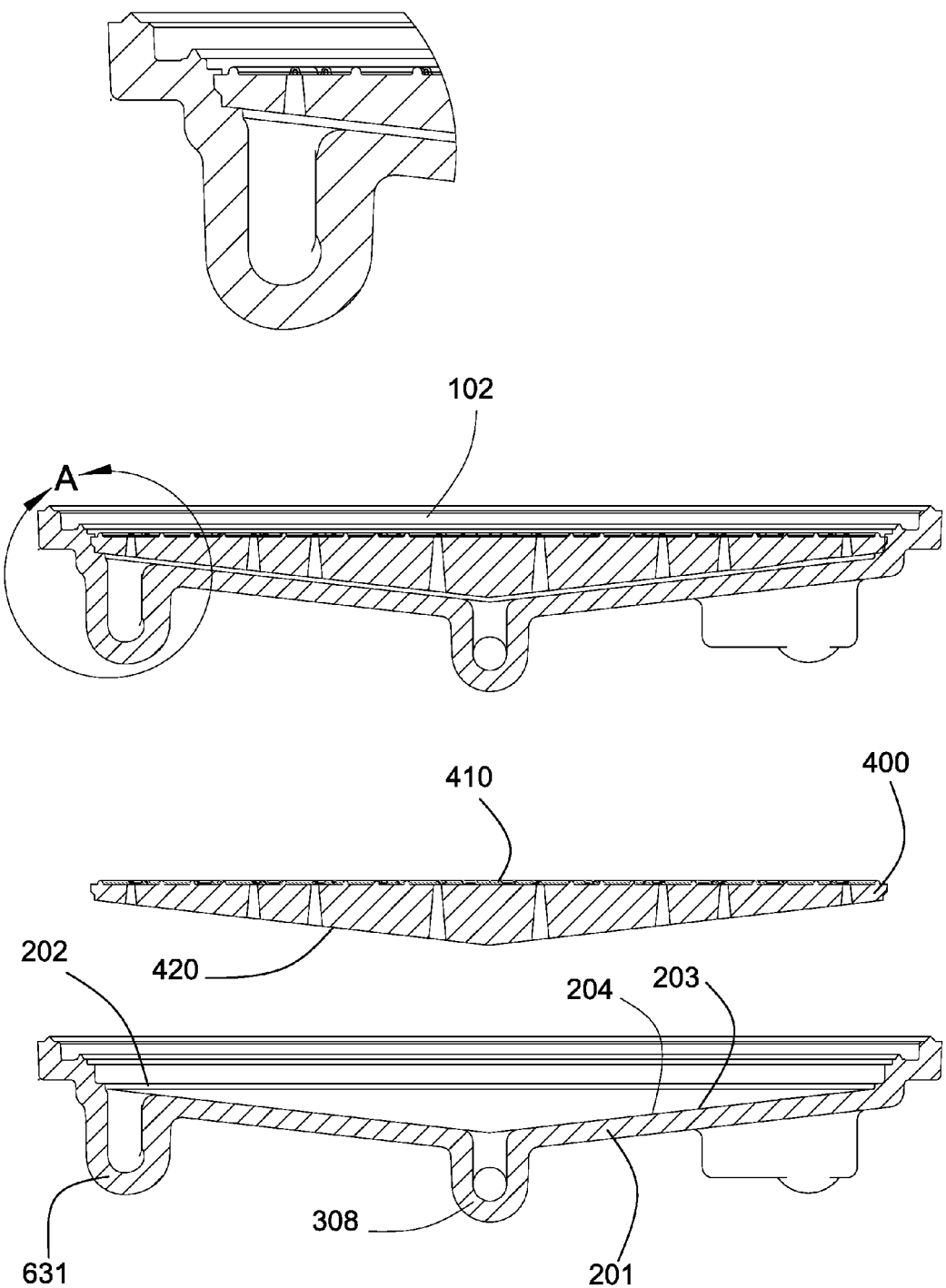

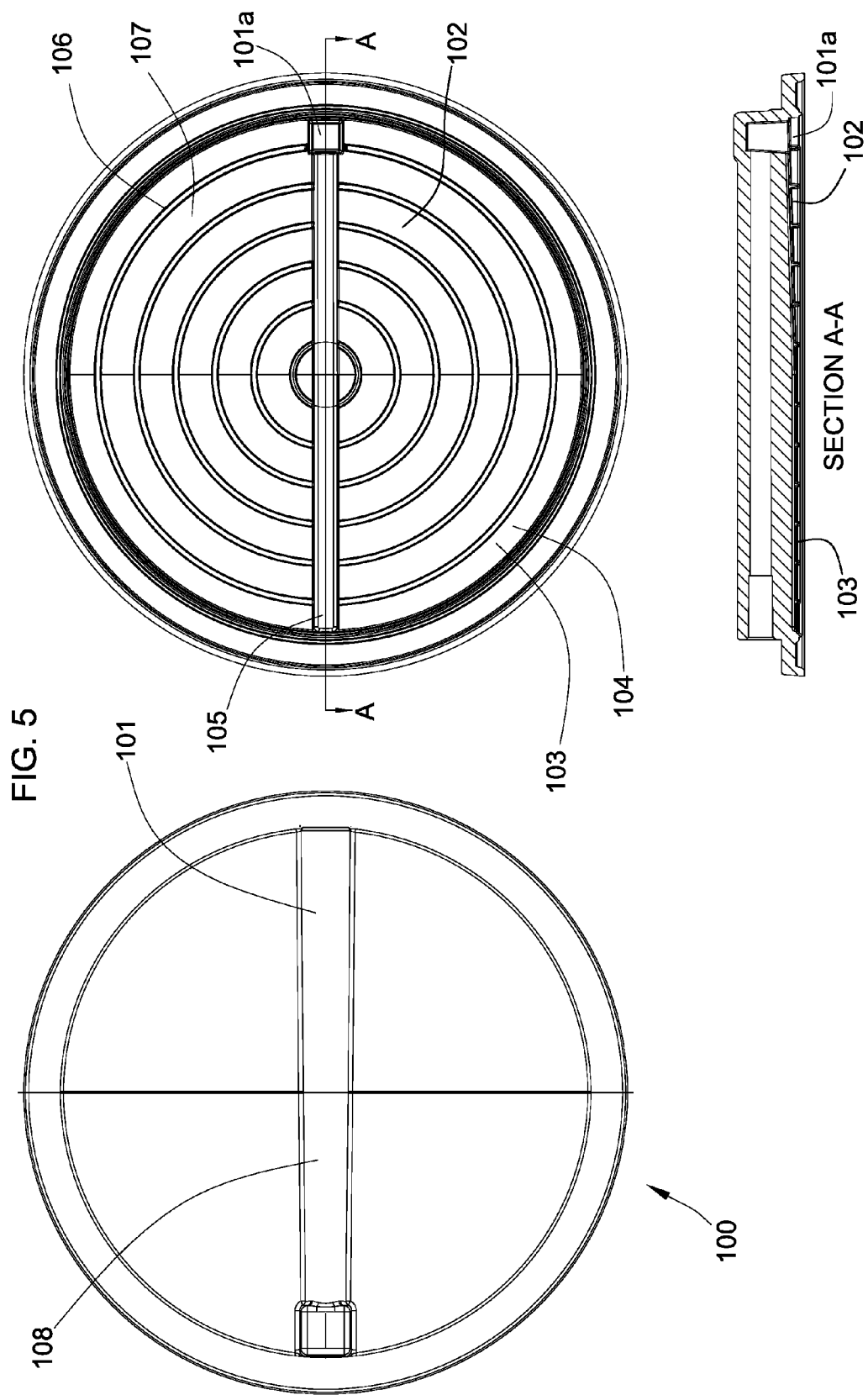

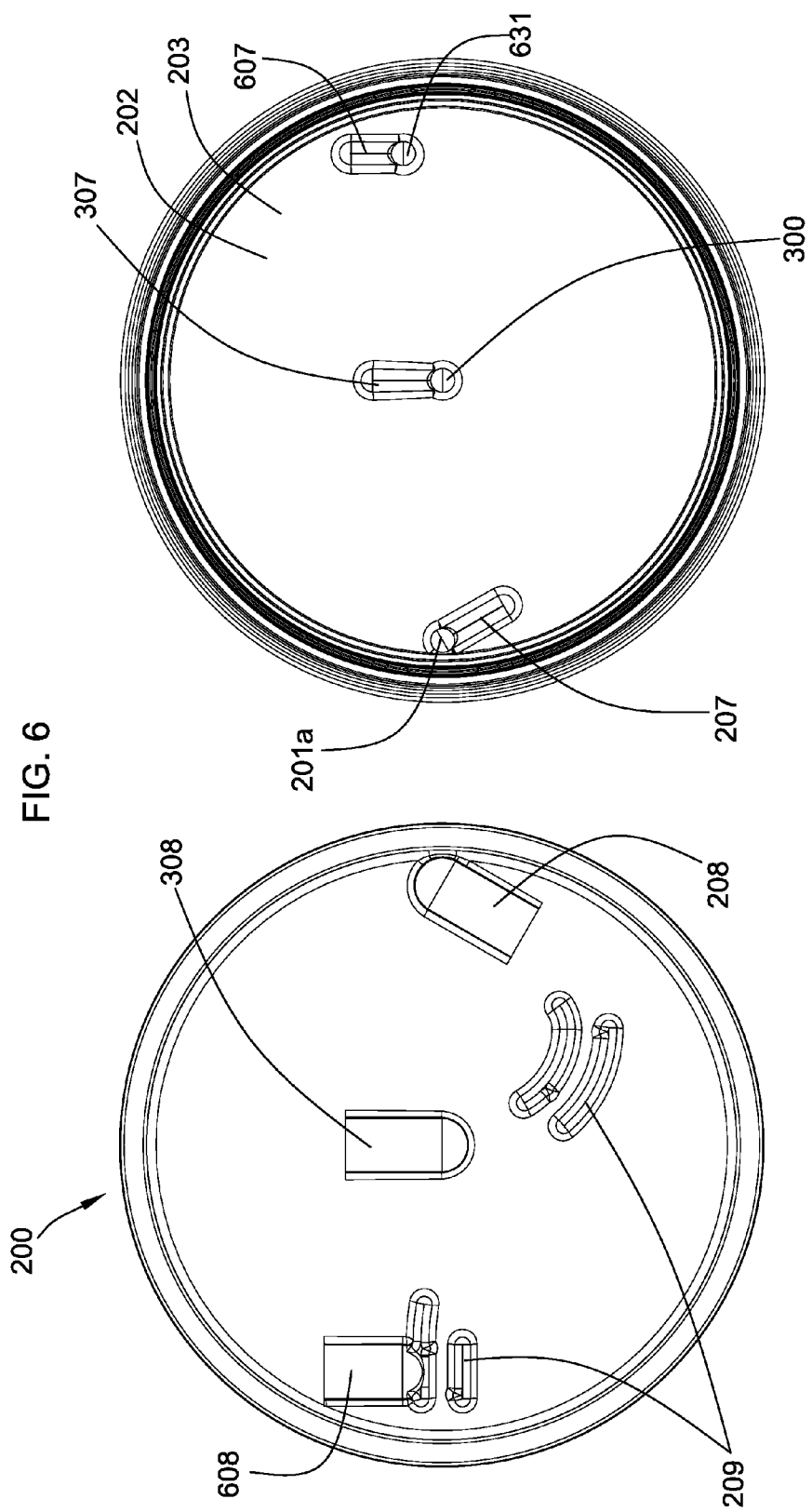

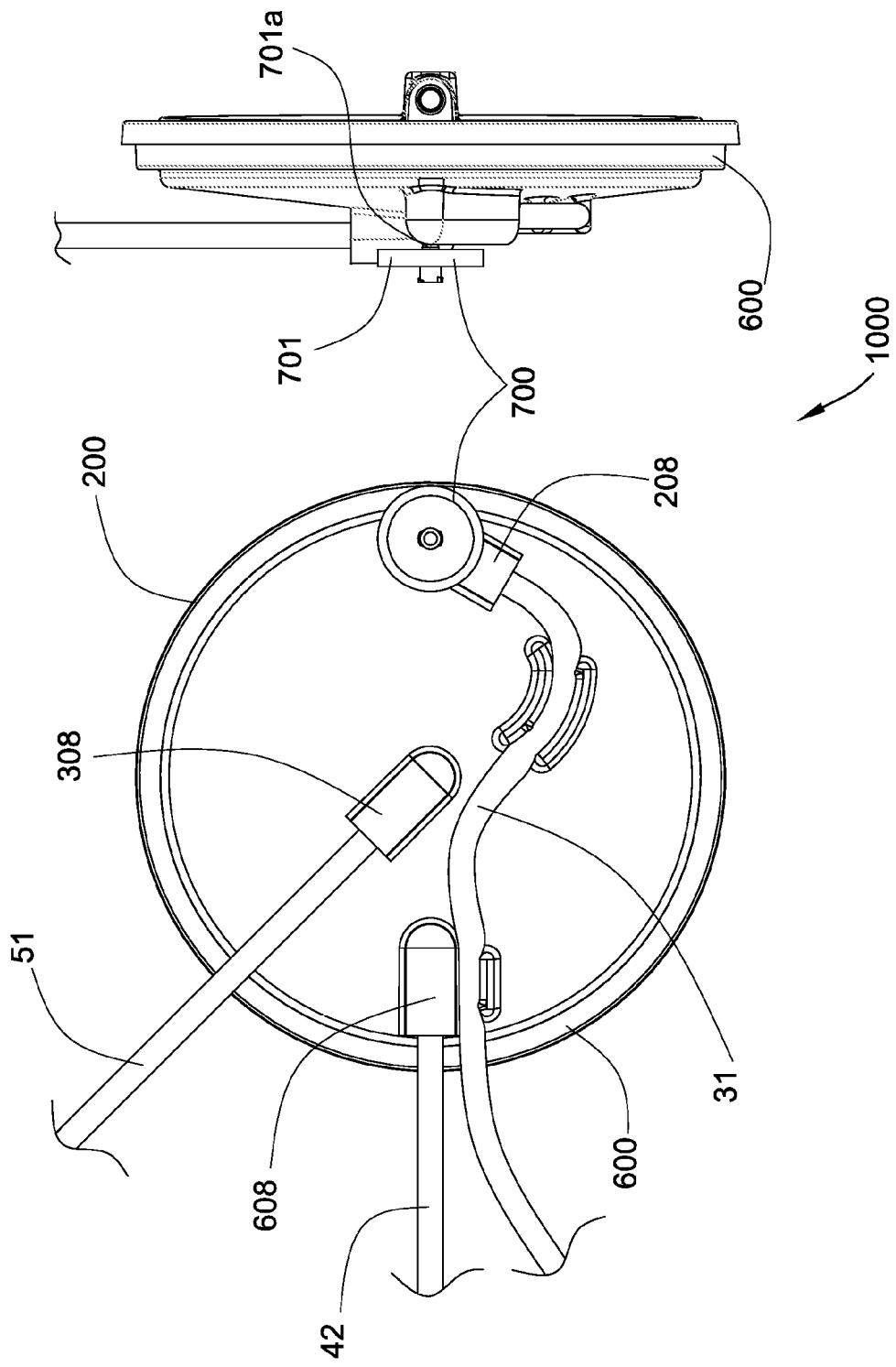

CELL HARVESTING DEVICE AND SYSTEM

BACKGROUND OF THE INVENTION

Desired target cells such as leukocytes and/or stem cells can be eluted from leukocyte depletion filters, and used in a variety of applications, including surgical use. However, methods for preparing these cells have suffered from drawbacks, such as labor intensiveness, cell contamination, and/or the inability to maintain a closed system.

The present invention provides for ameliorating at least some of the disadvantages of the prior art. These and other advantages of the present invention will be apparent from the description as set forth below.

BRIEF SUMMARY OF THE INVENTION

An embodiment of the invention provides a biological fluid processing device comprising (a) a housing comprising an inlet port and an outlet port and defining a fluid path between the inlet port and the outlet port, the housing further comprising an elution fluid inlet port and a drain port; (b) a porous fibrous leukocyte depletion filter having an upstream surface and a downstream surface, disposed in the housing across the fluid flow path; wherein the inlet port is upstream of the upstream surface of the leukocyte depletion filter, and, the outlet port, the elution fluid inlet port, and the drain port, are downstream of the downstream surface of the leukocyte depletion filter. Preferably, the device further comprises a perforated diffusing plate having a first surface and a second surface, disposed in the housing across the fluid flow path, wherein the diffusing plate is disposed in the housing between the downstream surface of the leukocyte depletion filter and the outlet.

In another embodiment, a biological fluid processing system is provided, comprising an embodiment of the biological fluid processing device, in fluid communication with at least one container, more preferably, at least two containers. In one embodiment of the system, one of the containers comprises a container suitable for cryopreservation of stem cells and/or leukocytes.

In an embodiment of a method according to the invention, a method for processing a biological fluid comprises passing the biological fluid through an embodiment of the biological fluid processing device, for example, (a) passing a biological fluid from a first container through a biological fluid processing device comprising a housing comprising an inlet port and an outlet port, and defining a fluid path between the inlet port and the outlet port, the housing further comprising an elution fluid inlet port and a drain port, and a porous fibrous leukocyte depletion filter having an upstream surface and a downstream surface, disposed in the housing across the fluid flow path; wherein the inlet port is upstream of the upstream surface of the leukocyte depletion filter, and the outlet port, the elution fluid inlet port, and the drain port, are downstream of the downstream surface of the leukocyte depletion filter; and passing leukocyte-depleted biological fluid from the outlet port into a second container; (b) passing gas through the outlet port and displacing biological fluid in the downstream chamber from the housing through the drain port into the second container or into a third container; and, (c) passing elution solution from an elution solution delivery device through the elution fluid inlet port, the leukocyte depletion filter, and the inlet port, into an eluted target cell container; wherein the elution solution elutes leukocytes and/or stern cells from the filter into the eluted target cell container.

In another embodiment, a method for processing a biological fluid comprises (a) passing a biological fluid from a first container through a biological fluid processing device comprising a housing comprising an inlet port and an outlet port and defining a fluid path between the inlet port and the outlet port, the housing further comprising an elution fluid inlet port and a drain port, and a porous fibrous leukocyte depletion filter having an upstream surface and a downstream surface, disposed in the housing across the fluid flow path; wherein the inlet port is upstream of the upstream surface of the leukocyte depletion filter, and the outlet port, the elution fluid inlet port, and the drain port, are downstream of the downstream surface of the leukocyte depletion filter; and passing leukocyte-depleted biological fluid from the outlet port into a second container; (b) passing gas from the second container through the outlet port and displacing biological fluid in the downstream chamber from the housing through the drain port into a third container; and (c) passing elution solution from an elution solution delivery device through the elution fluid inlet port, the leukocyte depletion filter, and the inlet port, into a fourth container; wherein the elution solution elutes leukocytes and/or stern cells from the filter into the fourth container. In a preferred embodiment, the method is carried out while maintaining a closed system.

BRIEF DESCRIPTION OF THE SEVERAL VIEWS OF THE DRAWING(S)

FIG. 1 shows a perspective view of an embodiment of a biological fluid processing device according to the present invention, comprising a first housing section including an inlet port, and a second housing section comprising an outlet port, an elution fluid inlet port, and a drain port, and also showing a leukocyte depletion filter and an optional diffusing plate between the first and second housing sections.

FIG. 2 shows perspective, side, and cross-sectional views of an embodiment of a diffusing plate for use in an embodiment of the filter device of the present invention.

FIG. 4 shows a partial cross-sectional view of embodiments of the diffusing plate and the outlet portion of a filter device housing according to the present invention.

FIG. 5 shows views of an inlet portion of an embodiment of a filter device housing according to the present invention.

FIG. 6 shows views of an outlet portion of an embodiment of a filter device housing according to the present invention.

Figure 7A:
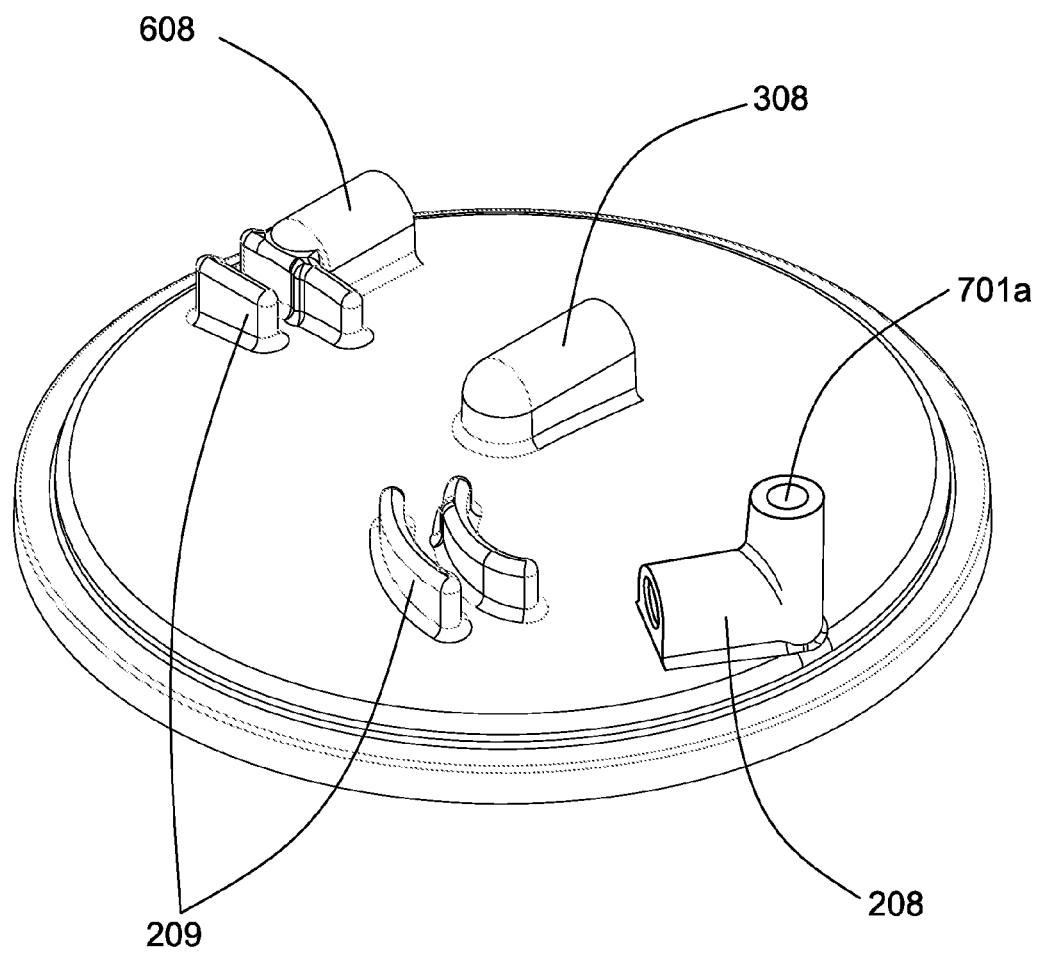

FIG. 7 shows a perspective view of other embodiments of a biological fluid processing device according to the present invention, wherein the second housing section comprises an outlet port, an elution fluid inlet port, a drain port, and a vent port (FIG. 7A), as well as showing conduits communicating with the outlet port, elution fluid inlet port, and drain port, as well as showing a vent device housing (FIG. 7B).

Figure 1:
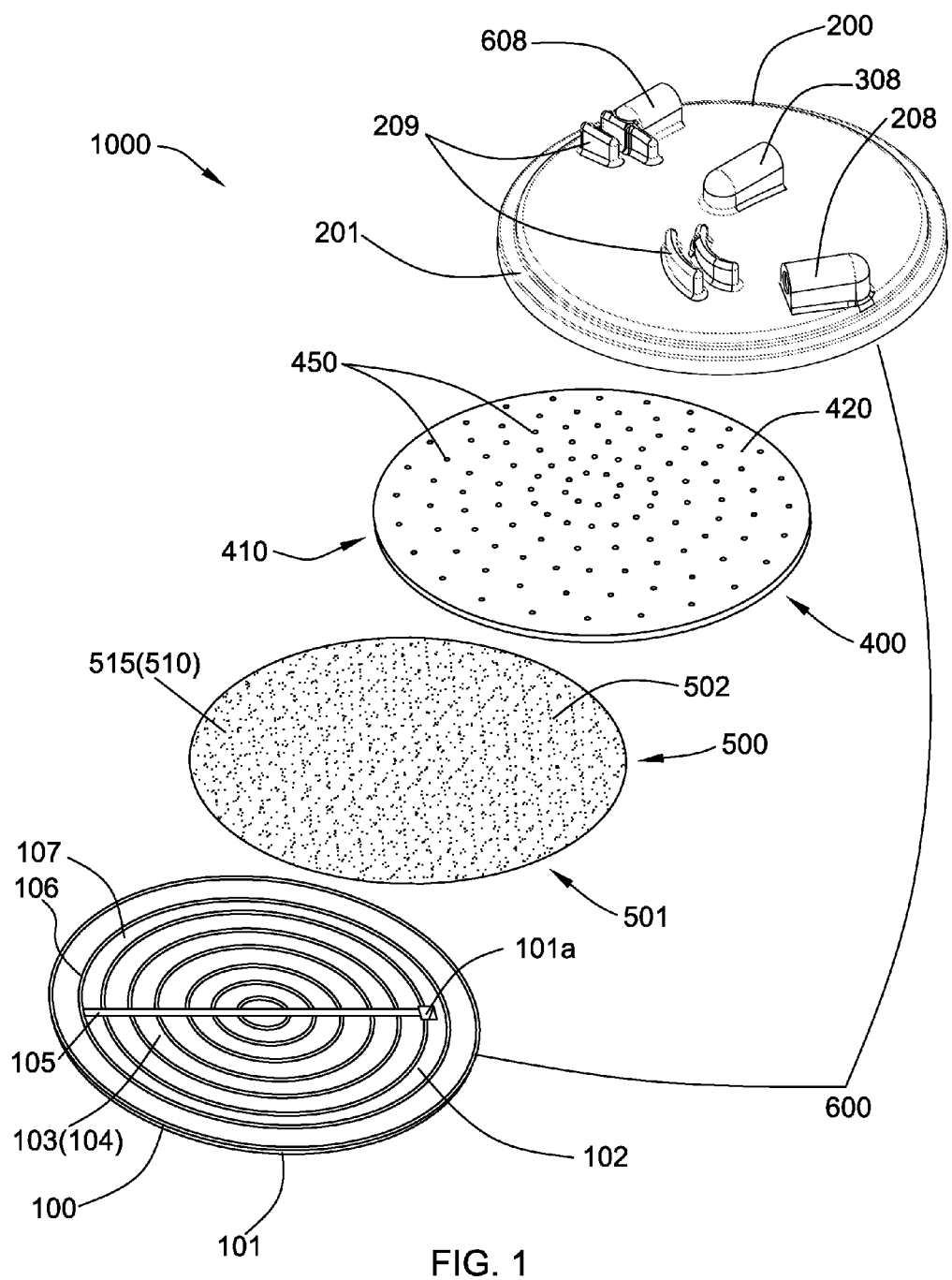
Figure 8:
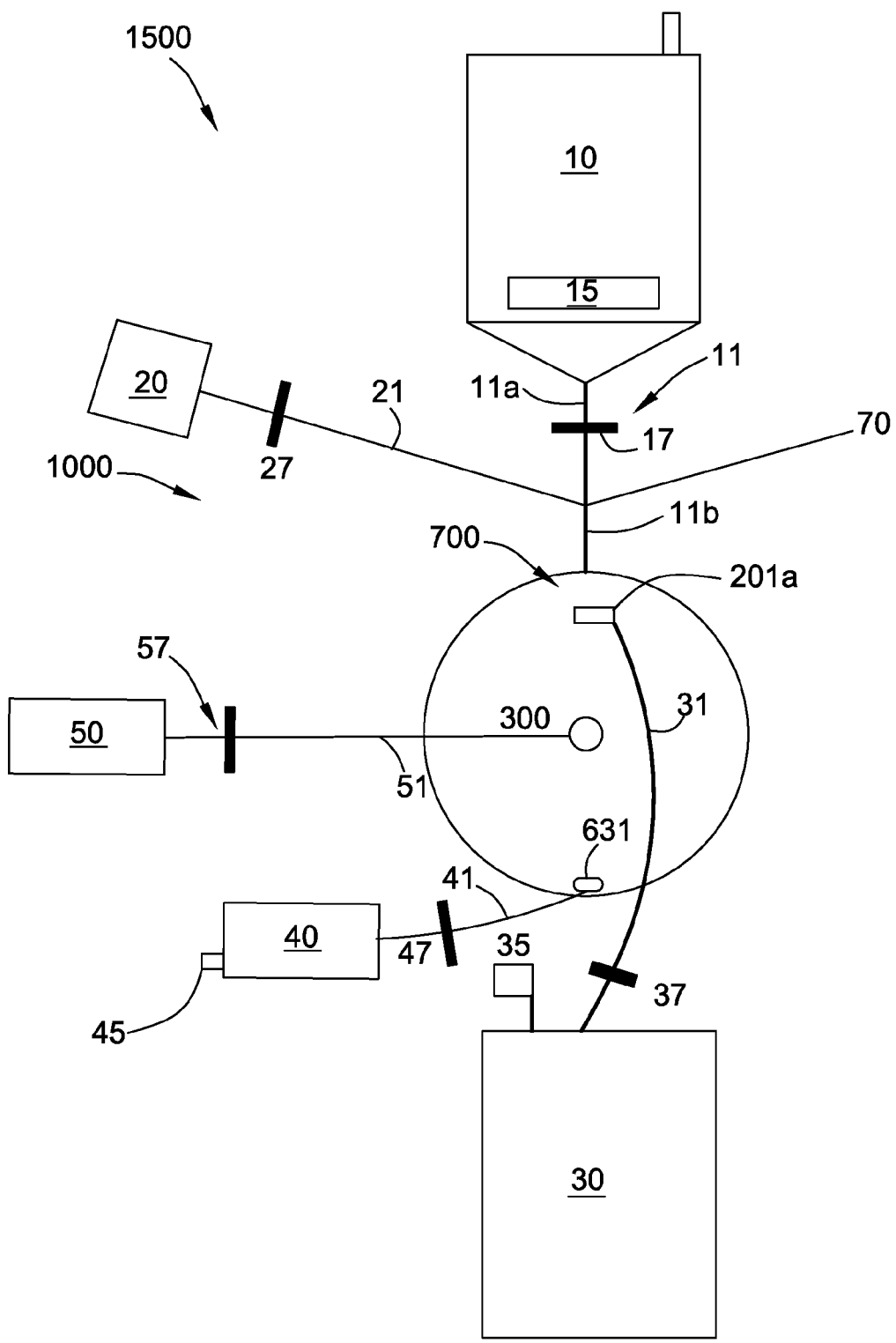

FIG. 8 shows an embodiment of a biological fluid processing system according to the present invention, wherein the system includes the embodiment of the biological fluid processing device shown in FIG. 1.

Figure 9:
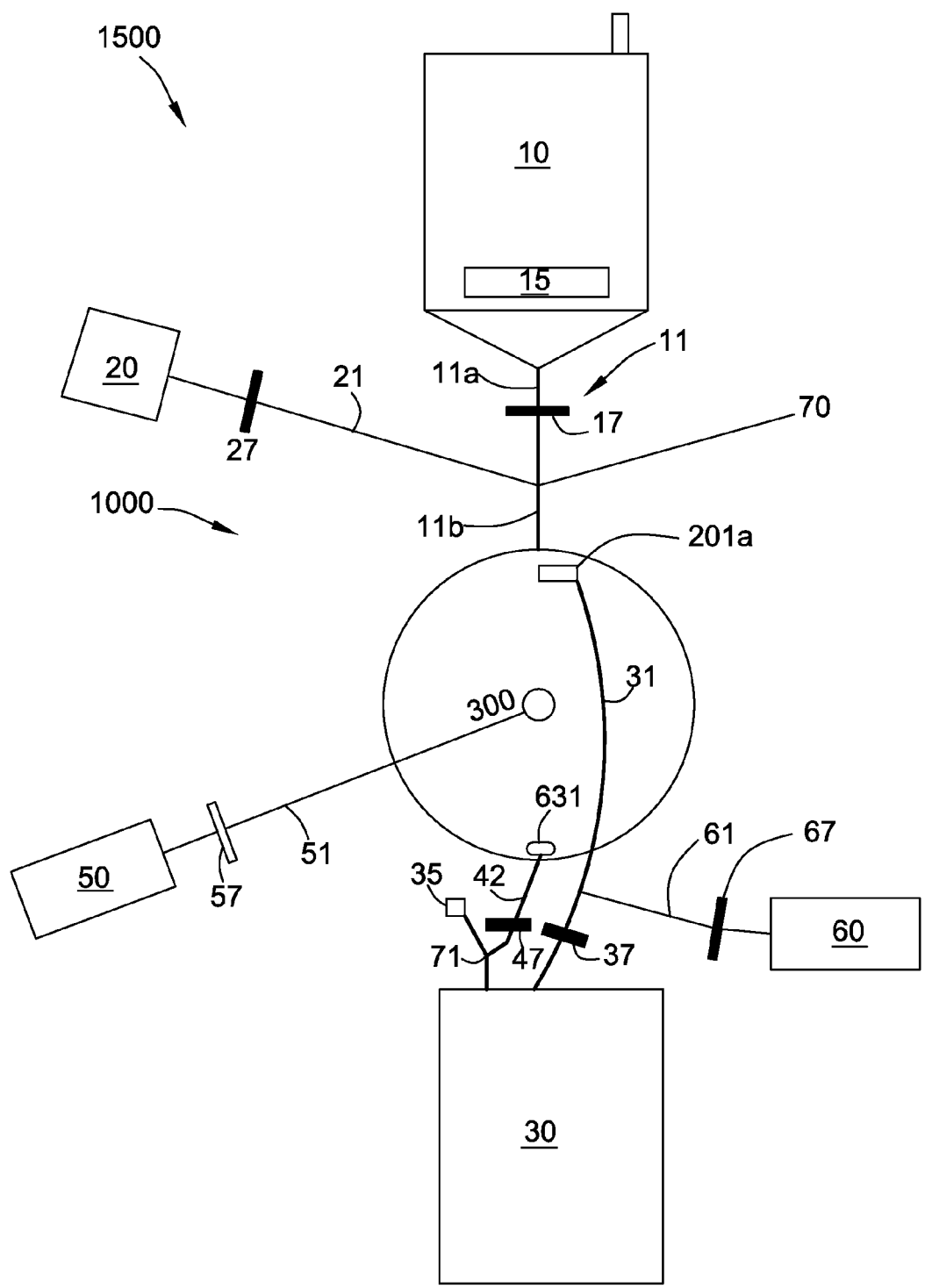

FIG. 9 shows another embodiment of a biological fluid processing system according to the present invention, wherein the system includes the embodiment of the biological fluid processing device shown in FIG. 1, as well as a gas collection container.

Figure 10:
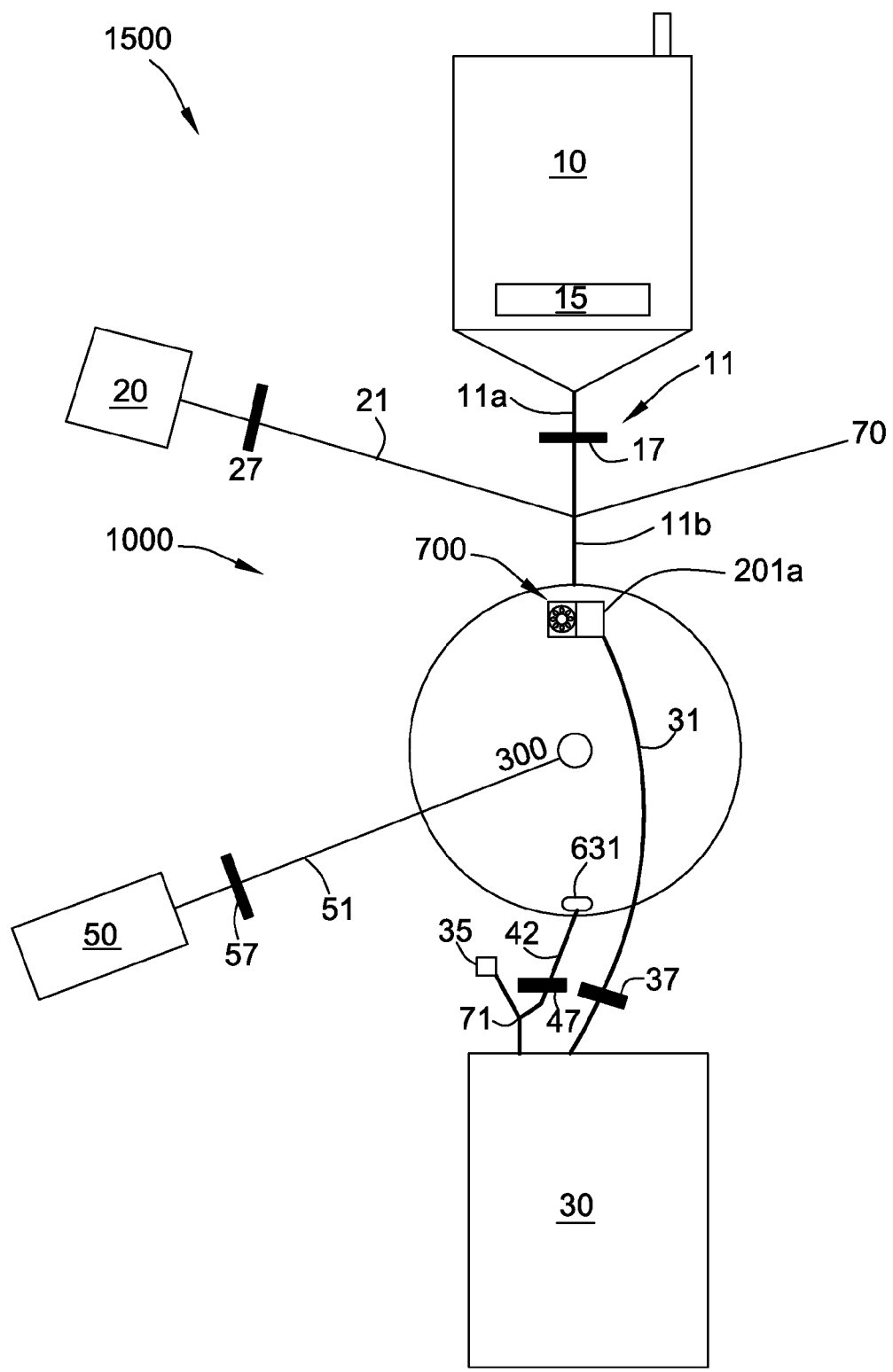

FIG. 10 shows another embodiment of a biological fluid processing system according to the present invention, wherein the system includes the embodiment of the biological fluid processing device including a vent device (e.g., as shown in FIG. 7B).

DETAILED DESCRIPTION OF THE INVENTION

Advantageously, desired biological fluid components, e.g., leukocytes and/or stem cells, can be recovered, and, if desired, concentrated in a volume of fluid (compared to the original concentration in the biological fluid), while reducing contamination by non-desired biological fluid components, e.g., red blood cells. Since contamination by red blood cells can be reduced, there is no need to carry out additional processing to remove the red blood cells, e.g., by centrifugation and/or lysis (e.g., via chemical treatment, such as with ammonium chloride). This additional processing is not only labor intensive, but can also be stressful to the desired biological fluid components to be harvested. Moreover, the desired cells can be recovered while maintaining a closed system, and this can be particularly desirable for use in, for example, a sterile field such as an operating room. Another advantage is that the systems and methods do not require an extra-system rinse fluid, though such a fluid can be utilized, if desired.

A biological fluid filter device according to an embodiment of the invention comprises (a) a housing comprising an inlet port and an outlet port and defining a fluid path between the inlet port and the outlet port, the housing further comprising an elution fluid inlet port and a drain port and defining a fluid flow path between the elution fluid inlet port and the inlet port; (b) a porous fibrous leukocyte depletion filter having an upstream surface and a downstream surface, disposed in the housing across the fluid flow paths; wherein the inlet port is upstream of the upstream surface of the leukocyte depletion filter, and, the outlet port, the elution fluid inlet port, and the drain port, are downstream of the downstream surface of the leukocyte depletion filter.

In an embodiment of the device, the housing has a wall downstream of the downstream surface of the leukocyte depletion filter, the wall includes the elution fluid inlet port, the outlet port, and the drain port, and the elution fluid inlet port is located between the outlet port and the drain port in the wall.

Preferably, the device further comprises at least one perforated diffusing plate having a first surface and a second surface, disposed in the housing across the fluid flow paths, preferably wherein the diffusing plate is disposed in the housing between the downstream surface of the leukocyte depletion filter and the outlet. In some embodiments, the device further comprises an additional perforated diffusing plate disposed in the housing between the upstream surface of the leukocyte depletion filter and the inlet.

In an embodiment of a method according to the invention, a method for processing a biological fluid comprises passing the biological fluid through an embodiment of the biological fluid filter device. For example, one embodiment of the method comprises (a) passing a biological fluid from a first container through a biological fluid filter device comprising a housing comprising an inlet port and an inlet chamber and an outlet port and a downstream chamber, and defining a fluid path between the inlet port and the outlet port, the housing further comprising an elution fluid inlet port and a drain port and defining a fluid flow path between the elution fluid inlet port and the inlet port, and a porous fibrous leukocyte depletion filter having an upstream surface and a downstream surface, disposed in the housing across the fluid flow paths; wherein the inlet port is upstream of the upstream surface of the leukocyte depletion filter, and the outlet port, the elution fluid inlet port, and the drain port, are downstream of the downstream surface of the leukocyte depletion filter; and passing leukocyte-depleted biological fluid from the outlet into a second container; (b) passing gas through the outlet port and displacing biological fluid in the downstream chamber from the housing through the drain port into the second container or into a third container; and, (c) passing elution solution from an elution solution delivery device through the elution fluid inlet port, the leukocyte depletion filter, and the inlet port, into an eluted target cell container; wherein the elution solution elutes leukocytes and/or stem cells from the filter into the eluted target cell container.

In an embodiment, the device further comprises at least one perforated diffusing plate having a first surface and a second surface, disposed in the housing across the fluid flow paths, and the diffusing plate is preferably disposed in the housing between the downstream surface of the leukocyte depletion filter and the outlet, and the method comprises passing elution solution from the elution solution delivery device through the elution fluid inlet port, the diffusing plate, the leukocyte depletion filter, and the inlet, into the eluted target cell container. In some embodiments, the device comprises first and second perforated diffusing plates, wherein the first diffusing plate is disposed in the housing between the downstream surface of the leukocyte depletion filter and the outlet, and the second diffusing plate is disposed in the housing between the upstream surface of the leukocyte depletion filter and the inlet, and the method comprises passing elution solution from the elution solution delivery device through the elution fluid inlet port, the first diffusing plate, the leukocyte depletion filter, the second diffusing plate, and the inlet, into the eluted target cell container.

Embodiments of the method comprise passing gas from the second container through the outlet port and displacing biological fluid in the downstream chamber from the housing through the drain port into the third container; or comprise passing leukocyte-depleted biological fluid from the outlet port including displacing gas into a gas collection container, and the method further comprises passing collected gas from the gas collection container through the outlet port and displacing biological fluid in the downstream chamber from the housing through the drain port into the second container; or comprise passing gas through a vent into the outlet port and displacing biological fluid in the downstream chamber from the housing through the drain port into the second container.

In another embodiment, a method for processing a biological fluid comprises (a) passing a biological fluid from a first container through a biological fluid filter device comprising a housing comprising an inlet port and an inlet (or upstream) chamber and an outlet port and a downstream chamber, and defining a fluid path between the inlet port and the outlet port, the housing further comprising an elution fluid inlet port and a drain port and defining a fluid flow path between the elution fluid inlet port and the inlet port, and a porous fibrous leukocyte depletion filter having an upstream surface and a downstream surface, disposed in the housing across the fluid flow paths; wherein the inlet port is upstream of the upstream surface of the leukocyte depletion filter, and the outlet port, the elution fluid inlet port, and the drain port, are downstream of the downstream surface of the leukocyte depletion filter; and passing leukocyte-depleted biological fluid from the outlet port into a second container; (b) passing gas from the second container through the outlet port and displacing biological fluid in the downstream chamber from the housing through the drain port into a third container; and (c) passing elution solution from an elution solution delivery device through the elution fluid inlet port, the leukocyte depletion filter, and the inlet port, into a fourth container; wherein the elution solution elutes leukocytes and/or stem cells from the filter into the fourth container.

In preferred embodiments of the method, the method is carried out while maintaining a closed system.

Embodiments of the invention also include biological fluid processing systems, the systems including an embodiment of the biological fluid filter device.

A biological fluid processing system according to an embodiment of the invention comprises (a) a biological fluid filter device; (b) a container for receiving leukocyte-depleted biological fluid, in fluid communication with the outlet port; (c) a container for receiving gas displaced biological fluid, in fluid communication with the drain port; and, (d) a container for receiving elution fluid and eluted leukocytes, in fluid communication with the inlet port. In some embodiments, the system further comprises an elution fluid delivery device, in fluid communication with the elution fluid inlet port and/or the system further comprises a biological fluid source container, in fluid communication with the inlet port. In one embodiment wherein the system further comprises an elution fluid delivery device, the device preferably comprises a syringe pump, or a prefilled syringe containing elution solution.

The invention can be carried out using biological fluid from a variety of sources, particularly mammals. It is preferred that the mammals are from the order Carnivora, including Felines (cats) and Canines (dogs), the order Artiodactyla, including Bovines (cows) and Swines (pigs) or of the order Perssodactyla, including Equines (horses). Typically, the mammals are of the order Primates, Ceboids, or Simoids (monkeys) or of the order Anthropoids (humans and apes). An especially preferred mammal is the human.

Each of the components of the invention will now be described in more detail below, wherein like components have like reference numbers.

As shown in more detail in FIGS. 1, 2, and 4-7, the illustrated embodiment of the biological fluid filter device 1000 comprises a housing 600 including a first housing section 100 comprising an inlet portion 101, an inlet port 101a (that can also comprise an elution fluid outlet port), an inlet chamber (or upstream chamber) 102, and an inlet portion wall 103 having an inner surface 104, an optional inlet channel 107 communicating with the inlet port 101a, and a second housing section 200 comprising an outlet portion 201, an outlet 208 communicating with outlet port 201a (shown in FIG. 6), a downstream chamber 202, and a downstream portion wall 203 having an inner surface 204, an optional outlet channel 207 communicating with the outlet port 201a (shown in FIG. 6), and defining a fluid flow path between the inlet port and the outlet port, and a porous fibrous leukocyte depletion filter 500 disposed in the housing across the fluid flow path, the filter having an upstream surface 501 and a downstream surface 502, the filter comprising at least one porous fibrous leukocyte depletion element 515 comprising at least one porous fibrous leukocyte depletion medium 510. The illustrated housing 600 also includes an elution tube 308 communicating with an elution fluid inlet port (or harvest port) 300 and an optional elution channel 307 communicating with the elution fluid inlet port (shown in FIG. 6), the housing defining a fluid flow path between the elution fluid inlet port and the inlet port, the illustrated housing also comprising a drain 608 communicating with a drain port 631, and an optional drain channel 607 communicating with the drain port (shown in FIG. 6), wherein the elution fluid inlet port and drain port are each downstream of the downstream surface of the filter.

For convenience, ports 201a and 300 are identified above as the outlet portion "outlet port" and "elution fluid inlet port" respectively; however, it should be clear that, for example, port 201a can comprise the outlet portion "elution fluid inlet port" and port 300 can comprise the outlet portion "outlet port" (and this is similarly applicable to the associated structures such as 207, 208, 307 and 308).

Preferably, as shown in FIGS. 1, 2, and 4, the device further comprises at least one perforated diffusing plate 400 comprising a first surface 410 and a second surface 420, and perforations 450, wherein the diffusing plate 400 and leukocyte depletion filter 500 are disposed in the housing across the fluid flow paths. However, in other embodiments, the device does not include a diffusing plate.

Optionally, e.g., as shown in FIG. 7B, the biological fluid filter device further comprises a vent device 700, comprising a vent housing 701 comprising a microporous vent element therein (not shown), shown attached to the second housing section 200, communicating with the outlet port 201a, wherein the vent device is attached at, and also communicates with, vent port 701a. In some embodiments, the vent device further comprises a removable cap.

The housing can include a variety of configurations including an inlet port, an outlet port, an elution fluid inlet port, a drain port, and defining a fluid flow path between the inlet port and the outlet port, and defining a fluid flow path between the elution fluid inlet port and the inlet port, wherein the leukocyte depletion filter (and, optionally, the diffusing plate) is disposed in the housing across the fluid flow paths.

In the illustrated embodiment shown in FIG. 6, the outlet port 201a, the elution fluid inlet port 301, and the drain port 631, are each arranged, in the same downstream portion wall 203 of the housing, wherein the elution fluid inlet port is located between the outlet port and the drain port, and the drain port is located at the lower part of the housing when the device is being used. However, other arrangements of the outlet port, elution fluid inlet port, and drain port are encompassed by the invention. For example, the drain port can be located in the side wall of the housing, downstream of the downstream surface of the filter. Typically, the elution fluid inlet port is located such that it opposes approximately the center of the downstream surface of the filter, the inlet port is located so that it opposes the upstream surface of the filter, but facing a more peripheral portion of the surface, rather than the center, and the outlet port is located so that it opposes the downstream surface of the filter, but facing a more peripheral portion of the surface, rather than the center.

If desired, the device can include one or more spacer and/or drainage components, e.g., as separate elements (such as, for example, mesh elements) and/or as part of the housing (such as one or more ridges on the surfaces of the housing facing the upstream and/or downstream surfaces of the filter). Such components may improve the flow of fluid through the filter device, e.g., for priming and/or for passing the biological fluid from the inlet through the filter and the outlet, and/or for passing the elution fluid from the elution fluid inlet port through the filter and the inlet.

In the illustrated embodiment shown in FIG. 5, the inlet portion 100 includes an inlet portion wall 103 including an inner surface 104, including a slot 105, and a plurality of concentric ridges 106 and channels 107, wherein the ridges and channels are interrupted by the slot. In this illustrated embodiment, the slot varies in depth, having a greater depth at the end near the inlet port 101a, than at the other end of the slot. The illustrated inlet portion also includes an inlet tube 108, leading to the inlet port 101a. The presence of ridges provides spacing between the inlet portion wall 103 and the first surface 501 of the filter, and may improve the flow of fluid through the filter device, e.g., for priming and/or for passing the elution fluid from the elution fluid inlet port through the filter and the inlet port.

In the illustrated embodiment shown in FIG. 6, the outlet portion 200 includes an outlet portion wall 203 including an inner surface 204. Typically, as shown in FIG. 4, the appearance of the inner surface 204 is generally complementary to the appearance of the second surface 420 of the plate 400, e.g., when the second surface 420 has a generally convex appearance, the inner surface 204 preferably has a generally concave appearance, and when the second surface 420 is generally planar, the inner surface 204 is generally planar.

Additionally, in the embodiment illustrated in FIG. 6, the outlet portion includes an outlet 208 leading to the outlet port 201a and optional outlet channel 207, an elution tube 308 leading to the elution fluid inlet port 300 and optional channel 307, a drain 608 leading to the drain port 631 and optional channel 607, as well as retainers 209 for retaining flexible conduits communicating with at least one of the tubes.

In the illustrated embodiment of the plate 400 in FIGS. 1, 2, and 4, the first surface 410 facing the leukocyte depletion filter has generally planar appearance, and the second surface 420 facing the housing outlet port has a generally convex appearance (e.g., gradually decreasing in thickness from the center to the periphery). However, other arrangements can be utilized.

Figure 3A:
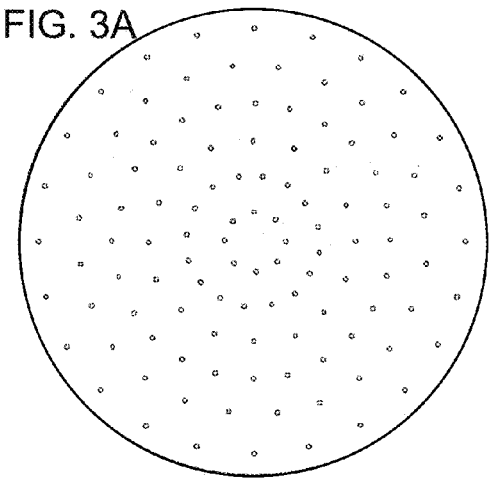
FIG. 3 shows a variety of illustrative diffusing plate perforation patterns and distributions (A-N).
Figure 3D:
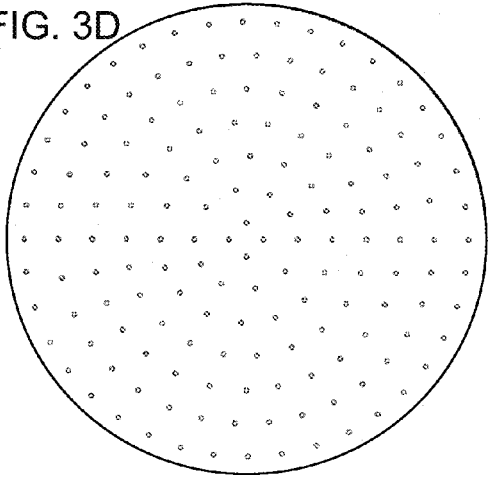
Figure 3B:
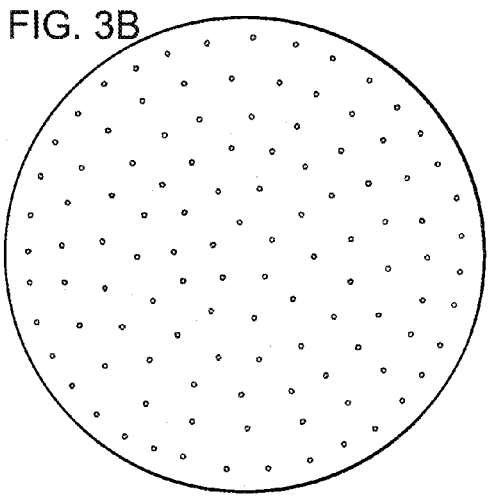
Figure 3E:
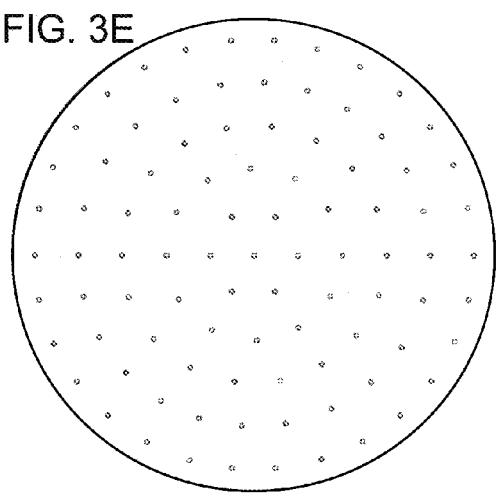
Figure 3C:
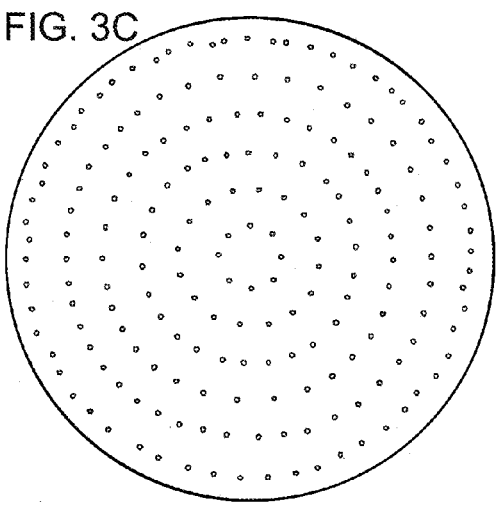
Figure 3F:
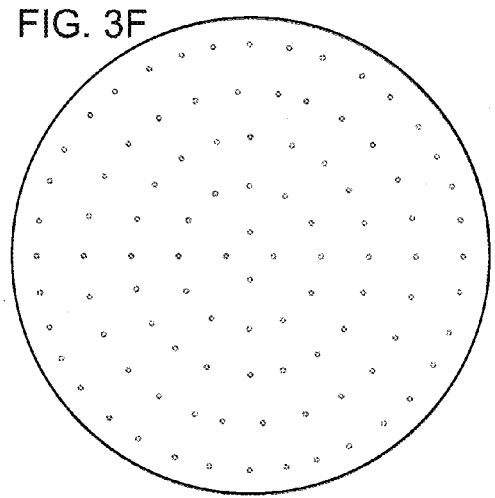
Figure 3G:
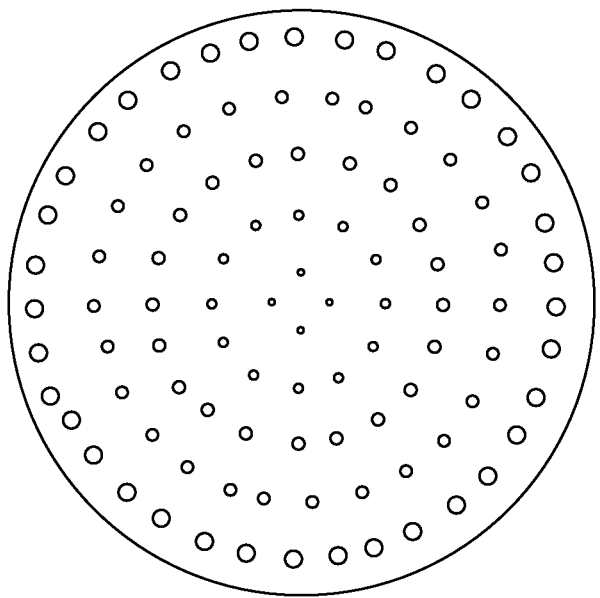
Figure 3H:
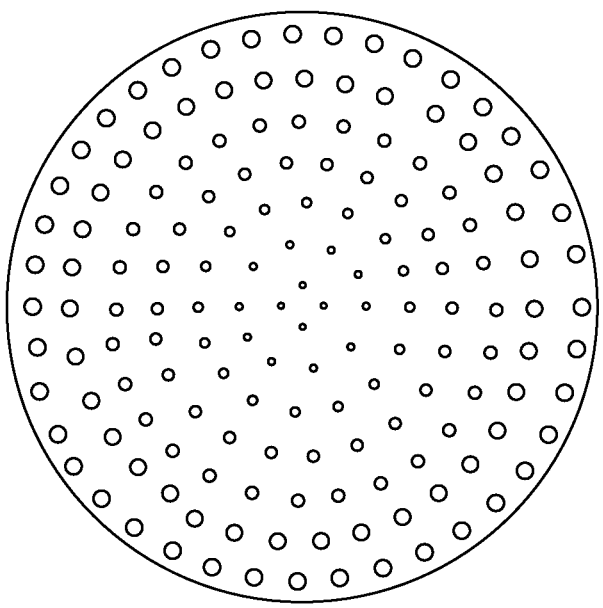
Figure 3I:
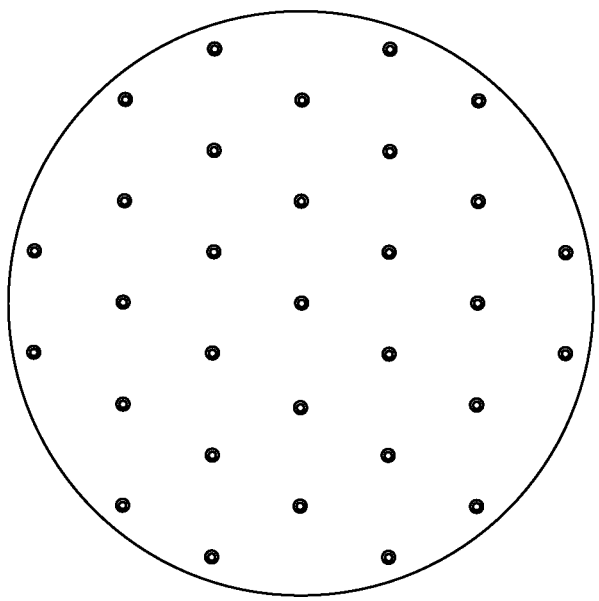
Figure 3J:
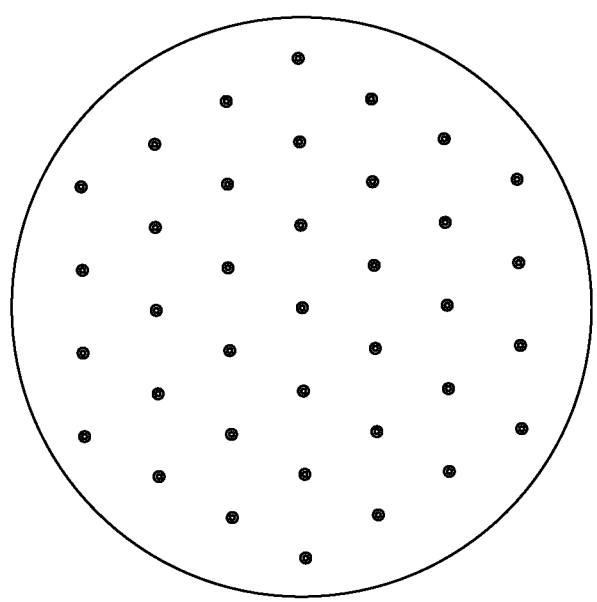
Figure 3K:
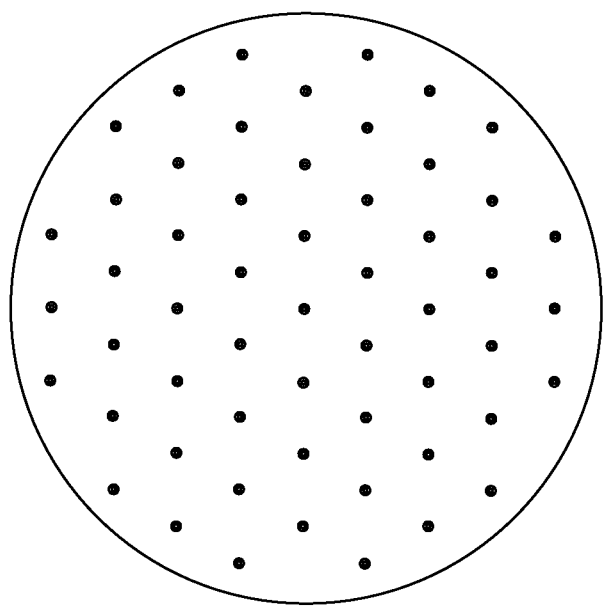
Figure 3L:
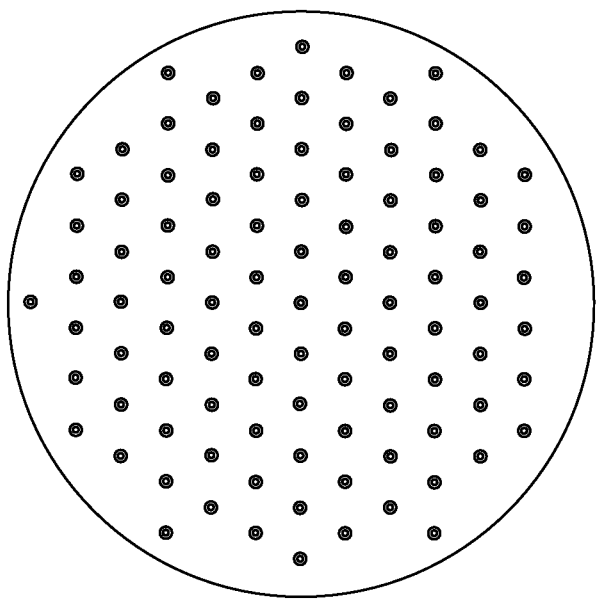
Figure 3M:
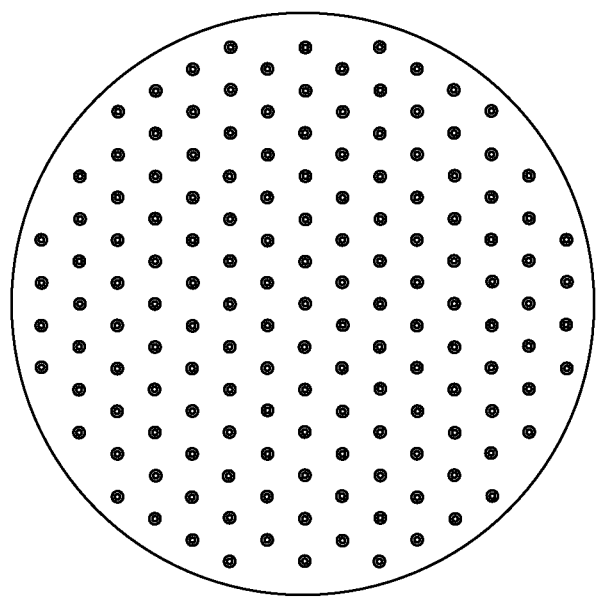
Figure 3N:
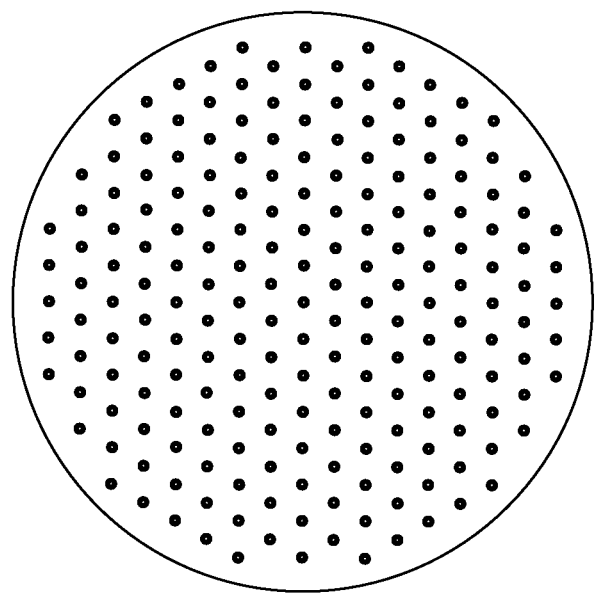

The perforations 450 in the plate 400 can be in any suitable pattern and distribution (e.g., illustrative patterns and distributions are shown in FIG. 3A-3N). Preferably, the perforations are arranged to direct elution fluid through as much of the filter medium as possible, while reducing elution fluid flow overlap through adjacent perforations, while the device (including the diffusing plate) provides a threshold of force of at least about 10 psig, preferably, at least about 15 psig, more preferably, at least about 20 psig. In some embodiments, the threshold of force is in the range of about 20 psig to about 45 psig.

In some embodiment wherein the plate(s) is/are circular, a plurality of perforations form a pattern of two or more generally concentric circles wherein the circles (formed by a plurality of perforations generally equidistant from the center of the plate) increase in diameter from the center toward the outer periphery of the plate. In some other embodiments, the plurality of perforations do not form generally concentric circles, or the patterns include a combination of generally concentric circles and non-circular patterns. In some of the illustrated embodiments, the perforations toward the outer periphery form generally concentric circles, wherein in some embodiments the perforations in and/or near the center form a generally concentric circle (e.g., as illustrated in FIGS. 3A and 3C), and in other embodiments, the central pattern differs from the pattern of the rest of the plate, e.g., the central pattern is not generally concentric (for example, as illustrated in FIGS. 3B, 3D, and 3F), or the plate can have few perforations in the center (e.g., FIG. 3E has a single perforation in the center).

In embodiments illustrated in FIGS. 3A and 3C, the perforations form a pattern of six generally concentric circles wherein the circles increase in diameter from the center toward the outer periphery of the plate. In some other illustrated embodiments (FIGS. 3B, and 3D-3F), the non-central part of the plate has generally concentric circles wherein the circles increase in diameter from the center toward the outer periphery of the plate. In some other illustrated embodiments (FIGS. 3I-3N), the perforations form different patterns (e.g., non-circular), and, for example, the perforations near the outer periphery of the plate have a different pattern (e.g., non-circular, with spaces between some of the perforations), than the perforations located at other portions of the plate.

The perforations can have any suitable inside diameter, and the plate(s) can have perforations of different diameter, e.g., wherein the diameters of the perforations in at least one portion (for example, an outer ring) differ from the diameters of the perforations in at least one other portion (for example, a more central ring). Illustratively, a more outer ring can have perforations having a larger average diameter than the average diameters of the perforations in a more central portion (e.g., as shown in FIGS. 3G and 3H), or vice versa. Typically, the average inside diameters of the individual perforations are in the range of from about 0.005 inches (about 0.1 mm), or less, to about 0.12 inches (about 3.0 mm), or more. The perforations can have substantially the same inner diameter from one surface to another, or, in the embodiment shown in the cross-sectional view of FIG. 2, the perforations can provide asymmetric openings, e.g., the perforations at the surface 420 have a larger internal diameter than the perforations at the surface 410. Alternatively, the perforations at the surface 410 can have a larger internal diameter than the perforations at the surface 420 (not shown).

Either or both surfaces of a plate can further include additional components, for example, ridges. Preferably, the first surface 410 of the plate facing the second surface 502 of the filter includes upwardly protruding ridges, e.g., to space the surfaces apart to improve the drainage of biological fluid from the filter during filtration. In the illustrated embodiment shown in FIG. 2, the surface 410 includes a plurality of concentric ridges 411, wherein the ridges are non-continuous, and alternating rows of ridges are interrupted by perforations 450. In the illustrated embodiment, the ridges form a pattern of twelve generally concentric circles wherein the circles increase in diameter from the center toward the outer periphery of the plate.

The plate(s), which is typically an integral, one-piece solid plate having perforations therein, can be any suitable shape, e.g., generally rectangular, square, circular, oval, or triangular. Typically, the shape of a plate will generally correspond to that of the interior of the housing, e.g., for ease of fitting and/or sealing in the housing. For example, in the illustrated embodiments, the housing and plate are generally circular.

A variety of leukocyte depletion filters are suitable for use in the invention. In the illustrated embodiment, the porous fibrous leukocyte depletion filter 500 comprises at least one porous fibrous leukocyte depletion element 515 comprising at least one porous fibrous leukocyte depletion medium 510, wherein the medium can comprise one or more layers of media. The filter can include a plurality of filter elements. The filter can include additional elements, layers, or components, that can have different structures and/or functions, e.g., at least one of prefiltration, support, drainage, spacing and cushioning. Illustratively, the filter can also include at least one additional element such as a mesh and/or a screen.

A variety of elution fluid delivery devices are suitable for use in the invention. In the illustrated embodiment of the system, the elution fluid delivery device 50 comprises a syringe (preferably, a prefilled syringe). Alternatively, for example, the elution fluid delivery device can comprise a syringe pump.

The desired components (e.g., retained cells, such as leukocytes and/or stem cells) captured or retained by the filter are released by backflushing from the porous fibrous leukocyte depletion filter, i.e., by passing the elution fluid from the elution fluid inlet port, through the porous filter in a direction from the downstream side towards the upstream side, and through an inlet portion port, such that the elution fluid containing the component(s) is passed from the inlet portion port into a target cell collection container communicating with the inlet portion port.

The backflushing can be accomplished at any suitable fluid flow rate, e.g., about 0.1-15 L/min/m$^2$, although flow rates significantly more or less than this range can be used. For example, backflushing can be accomplished at a fluid flow rate of about 0.5-10 L/min/m$^2$, such as about 1-8 L/min/m$^2$; more preferably the flow rate is about 1.5-7 L/min/m$^2$, such as about 2-6 L/min/m$^2$ or even about 2.5-5 L/min/m$^2$ (e.g., about 3-4 L ml/min/m$^2$). The most preferable flow rate may depend upon the viscosity and/or the temperature of the elution fluid, and the nature of the filter medium. Thus, in some applications, such as when more gentle treatment is desired, backflushing can be accomplished at a flow rate about 1-100 ml/min/m$^2$, (e.g., about 15-85 ml/min/m$^2$); more preferably the flow rate is about 30-70 ml/min/m$^2$ or even about 40-60 ml/min/m$^2$ (e.g., about 50 ml/min/m$^2$). Additionally, in some embodiments, the backflushing can include pulsing the flow of the backflushing fluid.

A variety of biological fluid elution fluids are suitable for use in the invention. Typically, the fluid is physiologically compatible with the desired biological fluid component(s), and does not substantially effect the component(s). Illustrative fluids include, for example, saline, as well as those fluids, including more viscous fluids, disclosed in U.S. Pat. Nos. 6,544,751 and 7,291,450.

In accordance with embodiments of the invention, any suitable volume of biological fluid can be processed, and the device can include a variety of filters, e.g., filters having diameters in the range from, for example, about 0.5 inches (about 1.2 cm), or less, to about 5 inches (about 12 cm), or more.

The following definitions are used in accordance with the invention.

Biological Fluid. A biological fluid includes any treated or untreated fluid associated with living organisms, particularly blood, including whole blood, warm or cold blood, cord blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); fluid derived from the placenta and/or the umbilical cord; blood products derived from blood or a blood component or derived from bone marrow; fluid including stem cells; amniotic fluid; red cells separated from plasma and resuspended in physiological fluid or a cryoprotective fluid; and platelets separated from plasma and resuspended in physiological fluid or a cryoprotective fluid. A biological fluid also includes a physiological solution comprising a bone marrow aspirate. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

As used herein, the term "closed" refers to a system that allows the collection and processing (and, if desired, the manipulation, e.g., separation of portions, separation into components, filtration, storage, and preservation) of biological fluid, e.g., donor blood, blood samples, and/or blood components, without the need to compromise the sterile integrity of the system. A closed system can be as originally made, or result from the connection of system components using what are known as "sterile docking" devices. Illustrative sterile docking devices are disclosed in, for example, U.S. Pat. Nos. 4,507,119, 4,737,214, and 4,913,756.

A variety of materials can be used, including synthetic polymeric materials, to produce the fibrous porous leukocyte depletion media of the filter elements according to the invention. Suitable synthetic polymeric materials include, for example, polybutylene terephthalate (PBT), polyethylene, polyethylene terephthalate (PET), polypropylene, polymethylpentene, polyvinylidene fluoride, polysulfone, polyethersulfone, nylon 6, nylon 66, nylon 6T, nylon 612, nylon 11, and nylon 6 copolymers, wherein polyesters, e.g., PBT and PET, are more preferred. Typically, the fibrous porous media are prepared from melt-blown fibers. For example, U.S. Pat. Nos. 4,880,548; 4,925,572, 5,152,905, and 6,074,869, disclose porous leukocyte depletion filters and filter elements prepared from melt-blown fibers.

A filter element can have any suitable pore structure, e.g., a pore size (for example, as evidenced by bubble point, or by $K_L$ as described in, for example, U.S. Pat. No. 4,340,479, or evidenced by capillary condensation flow porometry), a pore rating, a pore diameter (e.g., when characterized using the modified OSU F2 test as described in, for example, U.S. Pat. No. 4,925,572), or removal rating that reduces or allows the passage therethrough of one or more materials of interest as the fluid is passed through the element. While it is believed leukocytes are primarily removed by adsorption, they can also be removed by filtration. The pore structure can be selected to remove at least some level of leukocytes, while allowing the passing therethrough of desired components, e.g., at least one of plasma, platelets, and red blood cells. The pore structure used depends on the composition of the fluid to be treated, and the desired effluent level of the treated fluid.

The filter element can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869. Typically, the filter element has a CWST of greater than about 53 dynes/cm (about $53 \times 10^{-5}$ N/cm), more typically greater than about 58 dynes/cm, (about $58 \times 10^{-5}$ N/cm), and can have a CWST of about 66 dynes/cm (about $66 \times 10^{-5}$ N/cm) or more. In some embodiments, the element may have a CWST in the range from about 62 dynes/cm to about 115 dynes/cm (about 62 to about $162 \times 10^{-5}$ N/cm), e.g., in the range of about 80 to about 100 dynes/cm (about 80 to about $100 \times 10^{-5}$ N/cm).

The surface characteristics of the element can be modified (e.g., to affect the CWST, to include a surface charge, e.g., a positive or negative charge, and/or to alter the polarity or hydrophilicity of the surface) by wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, vapor plasma, corona discharge, heat, a Van der Graff generator, ultraviolet light, electron beam, or to various other forms of radiation, or by surface etching or deposition using a plasma treatment.

In those embodiments including a vent, e.g., attached to the device housing or as a separate component of the system (e.g., a vent device comprising a housing and at least one vent element disposed in the housing), a variety of materials are suitable for use as vent elements. Suitable elements, including hydrophilic microporous membranes and hydrophobic porous membranes, and vent devices, are disclosed in, for example, U.S. Pat. Nos. 5,126,054 and 5,451,321. Preferably, when used in accordance with a closed system, the vent prevents the passage of bacteria therethrough, e.g., the vent includes a vent element having a bacterial blocking pore rating.

The housing can be sealed as is known in the art, utilizing, for example, an adhesive, a solvent, laser welding, radio frequency sealing, ultrasonic sealing and/or heat sealing. Additionally, or alternatively, the housing can be sealed via injection molding.

The housing and diffusing plate(s) can be any suitable shape, e.g., generally rectangular, square, circular, oval, or triangular. The housing and diffusing plate(s) can be fabricated from any suitable rigid impervious material, including any impervious thermoplastic material, which is compatible with the biological fluid being processed. In a preferred embodiment, the housing and diffusing plate(s) are fabricated from a polymer (the housing and diffusing plates can be fabricated from different polymers), such as an acrylic, polypropylene, polystyrene, or a polycarbonated resin, which may be a transparent or translucent polymer. Such housings and diffusing plates are easily and economically fabricated. In those embodiments wherein the housing is fabricated from a polymer that is transparent or translucent, the housing allows observation of the passage of the biological fluid through the housing.

Embodiments of the device can be included in a variety of biological fluid processing systems comprising a plurality of containers and a plurality of conduits, typically further comprising at least one conduit connector, and a plurality of flow control devices. Typically, a source container containing biological fluid to be processed is connected to an embodiment of a biological fluid processing system according to the invention. If desired, however, the biological fluid processing system can include the source container.

Preferably, the containers are flexible containers such as blood bags (e.g., collection bags and/or satellite bags). In one preferred embodiment, a system according to the invention comprises a closed system. A wide variety of suitable containers, conduits, connectors, and flow control devices (e.g., clamps and/or in-line devices such as transfer leg closures and/or valves) are known in the art. For example, blood collection and satellite bags, and conduits, can be made from plasticized polyvinyl chloride. Bags and/or conduits can also be made from, for example, ethylene butyl acrylate copolymer (EBAC) resin, ethylene methyl acrylate copolymer (EMAC) resin, plasticized ultra-high-molecular weight PVC resin, and ethylene vinyl acetate (EVA). The bags and/or conduits can also be formed from, for example, polyolefin, polypropylene, polyurethane, polyester, and polycarbonate and combinations of materials.

In those embodiments of a biological fluid processing system including a gas collection container, the gas collection container can comprise a flexible container as described above. Other suitable materials include ethylene and an acrylate, polyvinylidene fluoride (PVDF), and polytetrafluoroethylene (PTFE). The gas collection container (or "gas collection pouch") typically comprises a flexible film forming flexible side walls (in some embodiments, flexible resilient or flexible semi-resilient side walls), and the container has at least at least one port allowing gas to enter and/or leave the container. The flexible side walls can expand when air displaced by the biological fluid enters the bag and the walls can partially collapse when the port (or the conduit leading to the port) is opened and air passes from the container and through the port.

In those embodiments including cryopreservation of the desired biological fluid components (e.g., leukocytes and/or stem cells), suitable additional system components, e.g., containers and conduits compatible with cryopreservatives such as dimethyl sulfoxide (DMSO), and/or compatible with cryopreservation, include, but are not limited to, those disclosed in U.S. Pat. Nos. 6,146,124, and 5,789,147, U.S. Patent Application Publication 2004/0254560, and Canadian Patent Application 2259878.

Other system components include, for example, filters (e.g., for removing clots and/or debris from biological fluid and/or for providing sterile cryopreservative), and syringes, as is known in the art.

In the illustrated embodiment of the biological fluid processing system shown in FIGS. 8-40, the system 1500 comprises a biological fluid filter device 1000, in fluid communication, via conduits, with a container for filtered biological fluid (or effluent bag) 30, an eluted target cell (or harvested cell) container 20, and an elution fluid delivery device 50. As noted above, the system can include a source container for biological fluid to be processed, illustrated in FIG. 8 as source container (or influent bag) 10, shown with an optional filter element (a coarse element such as a screen element, e.g., for removing clots and/or debris) 15.

The illustrated embodiment of the system shown in FIG. 8 also includes a drain container 40, the illustrated embodiment of the system shown in FIG. 9 also includes a gas (or air) collection container 60, and the illustrated embodiment of the system shown in FIG. 10 also includes a vent device 700, shown attached to the biological fluid filter device.

Preferably, one or more of the containers further comprise ports such as sampling ports (more preferably, wherein the sampling ports comprise valved ports), and in the illustrated embodiment, the container for filtered biological fluid 30 includes an optional sampling port 35, and the drain container 40 includes an optional sampling port 45.

As noted above, embodiments of the system include a plurality of conduits, and preferably, at least one conduit connector, and a plurality of flow control devices. The illustrated embodiment of the system shown in FIG. 8 includes conduits 11 (shown as conduits 11a, and 11b), 21, 31, 41, and 51, connector 70, and a plurality of flow control devices 17, 27, 37, 47, and 57, such as clamps, associated with one or more of the conduits.

The illustrated embodiment of the system shown in FIG. 9 includes conduits 11 (shown as conduits 11a, and 11b), 21, 31, 42, 51, and 61, connectors 70, 71, and a plurality of flow control devices 17, 27, 37, 47, 57, and 67, such as clamps, associated with one or more of the conduits.

The illustrated embodiment of the system shown in FIG. 10 includes conduits 11 (shown as conduits 11a, and 11b), 21, 31, 42, and 51, connectors 70, 71, and a plurality of flow control devices 17, 27, 37, 47, and 57, such as clamps, associated with one or more of the conduits.

Using the illustrative system 1500 shown in FIG. 8 for reference, in one embodiment of the method, the biological fluid to be processed, e.g., bone marrow, is collected in source container (or influent bag) 10, and the container 10 is connected, preferably via sterile docking, to conduit 11 (conduit 11a), thus maintaining a closed system. Flow control devices 17, 27, 37, 47, and 57, e.g., slide clamps, are initially closed. The system is hung vertically, e.g., as illustrated in the Figure.

Flow control device 37, associated with conduit 31 between the outlet 201 of the filter device 1000 and the container for filtered biological fluid (or effluent bag) 30, is opened, followed by opening flow control device 17, associated with conduit 11a between the influent bag 10 and the inlet 101 of the filter device 1000.

The biological fluid is optionally prefiltered as it passes through the optional filter element 15 in influent bag 10, and the fluid is subsequently depleted of the components of interest, e.g., target cells (preferably, leukocytes and/or stem cells) as the fluid passes through the leukocyte depletion filter 500. The target cell-depleted (e.g., leukocyte- and/or stem cell-depleted) biological fluid (along with displaced gas) passing from the outlet port 201a and along conduit 31 is collected in the effluent bag 30. Once filtration is complete, and the upstream (inlet) chamber 102 of the filter device 1000 is empty, flow control device 17 is closed. The effluent bag 30 can include a sampling port 35, more preferably a valved sampling port, allowing samples to be taken from the container when desired, while maintaining a closed system.

Flow control device 47, associated with the conduit 41 between the drain container 40, and the drain port 631, is opened, and flow control device 37 remains open. Force is applied to the effluent bag 30 (e.g., by squeezing the container) such that gas in the container is directed through the outlet port 201a into the downstream chamber 202. Since the leukocyte depletion filter 500 has been wetted by the biological fluid, it will resist the passage of gas therethrough, and thus, biological fluid in the downstream chamber 202 will be displaced from the chamber through the drain port 631 into drain container 40. The drain container 40 can include a sampling port 45, more preferably a valved sampling port, allowing samples to be taken from the container when desired, while maintaining a closed system.

Flow control devices 37 and 47 are closed. Flow control device 27, associated with the conduit 21 between the eluted target cell container 20, and the connector for conduits 11a and 11b, and flow control device 57, associated with conduit 51, are opened. The elution fluid delivery device 50 (e.g., a syringe prefilled with elution solution) is operated, passing elution fluid via the elution fluid inlet port 300, through the porous fibrous leukocyte depletion filter 500 and porous fibrous leukocyte depletion medium 510 via the downstream surface 502 and the upstream surface 501, the inlet port 101a, and into the target cell container 20 via conduits 11b and 21. As the fluid passes through the porous fibrous leukocyte depletion filter 500, target cells are eluted, passing with the elution fluid into the target cell container 20. Flow control devices 27 and 57 are closed. Subsequently, target cell container 20 is disconnected from the system 1500, preferably, while maintaining a closed system.

Using the illustrative system 1500 shown in FIG. 9 for reference, in another embodiment of the method, the biological fluid to be processed, e.g., bone marrow, is collected in source container (or influent bag) 10, and the container 10 is connected, preferably via sterile docking, to conduit 11 (conduit 11a), thus maintaining a closed system. Flow control devices 17, 27, 37, 47, 57, and 67, e.g., slide clamps, are initially closed. The system is hung vertically, e.g., as illustrated in the Figure.

Flow control device 67, associated with conduit 61 communicating with gas collection container 60 is opened, and flow control device 37, associated with conduit 31 between the outlet 201 of the filter device 1000 and the container for filtered biological fluid (or effluent bag) 30, remains closed. Flow control device 17, associated with conduit 11a between the influent bag 10 and the inlet 101 of the filter device 1000, is opened.

The biological fluid is optionally prefiltered as it passes through the optional filter element 15 in influent bag 10, and the fluid is subsequently depleted of the components of interest, e.g., target cells (preferably, leukocytes and/or stem cells) as the fluid passes through the leukocyte depletion filter 500. The target cell-depleted (e.g., leukocyte- and/or stem cell-depleted) biological fluid passes from the outlet port 201a and along conduit 31, displacing gas ahead of the biological fluid. Since flow control device 37 remains closed, displaced gas passes along conduit 61 into gas collection container 60. After sufficient displaced gas passes into gas collection container 60, flow control device 67 is closed, and flow control device 37 is opened, allowing target cell-depleted fluid to pass into the effluent bag 30.

Once filtration is complete, and the upstream (inlet) chamber 102 of the filter device 1000 is empty, flow control device 17 is closed, and flow control device 37 is also closed.

Flow control devices 67 (associated with conduit 61) and 47 (associated with conduit 42; shown as conduits 42a and 42b) are opened.

Force is applied to the gas collection container 60 (e.g., by squeezing the container) such that gas in the container is directed along conduits 61 and 31 through the outlet port 201a into the downstream chamber 202. Since the leukocyte depletion filter 500 has been wetted by the biological fluid, it will resist the passage of gas therethrough, and thus, biological fluid in the downstream chamber 202 will be displaced from the chamber through the drain port 631 into the effluent container 30. The effluent container 30 can include a sampling port 35, more preferably a valved sampling port, allowing samples to be taken from the container when desired, while maintaining a closed system.

Flow control devices 47 and 67 are closed. Flow control device 27, associated with the conduit 21 between the eluted target cell container 20, and the connector for conduits 11a and 11b, and flow control device 57, associated with conduit 51, are opened. The elution fluid delivery device 50 (e.g., a syringe prefilled with elution solution) is operated, passing elution fluid via the elution fluid inlet port 300, through the porous fibrous leukocyte depletion filter 500 and porous fibrous leukocyte depletion medium 510 via the downstream surface 502 and the upstream surface 501, the inlet port 101a, and into the target cell container 20 via conduits 11b and 21. As the fluid passes through the porous fibrous leukocyte depletion filter 500, target cells are eluted, passing with the elution fluid into the target cell container 20. Flow control devices 27 and 57 are closed. Subsequently, target cell container 20 is disconnected from the system 1500, preferably, while maintaining a closed system.

Using the illustrative system 1500 shown in FIG. 10 for reference, in another embodiment of the method, the biological fluid to be processed, e.g., bone marrow, is collected in source container (or influent bag) 10, and the container 10 is connected, preferably via sterile docking, to conduit 11 (conduit 11a), thus maintaining a closed system. Flow control devices 17, 27, 37, 47, and 57, e.g., slide clamps, are initially closed, as is the vent device 700 (e.g., via a cap over the vent port). The system is hung vertically, e.g., as illustrated in the Figure.

Flow control device 37, associated with conduit 31 between the outlet 201 of the filter device 1000 and the container for filtered biological fluid (or effluent bag) 30, is opened, followed by opening flow control device 17, associated with conduit 11a between the influent bag 10 and the inlet 101 of the filter device 1000.

The biological fluid is optionally prefiltered as it passes through the optional filter element 15 in influent bag 10, and the fluid is subsequently depleted of the components of interest, e.g., target cells (preferably, leukocytes and/or stem cells) as the fluid passes through the leukocyte depletion filter 500. The target cell-depleted (e.g., leukocyte- and/or stem cell-depleted) biological fluid (along with displaced gas) passing from the outlet port 201a is collected in the effluent bag 30. Once filtration is complete, and the upstream (inlet) chamber 102 of the filter device 1000 is empty, flow control device 17 is closed. Flow control device 37 is closed.

Flow control device 47, associated with the conduit 42 between the effluent container 30, and the drain port 631, is opened. Vent device 700 is opened (e.g., by removing a cap covering the vent port), allowing gas from the external environment to pass through the vent element, through the vent port 701a, the outlet port 201a, and into the downstream chamber 202. Since the leukocyte depletion filter 500 has been wetted by the biological fluid, it will resist the passage of gas therethrough, and thus, biological fluid in the downstream chamber 202 will be displaced from the chamber through the drain port 631 into the effluent container 30.

The effluent container 30 can include a sampling port 35, more preferably a valved sampling port, allowing samples to be taken from the container when desired, while maintaining a closed system.

Flow control devices 37 and 47 are closed (in those embodiments wherein the vent device does not automatically prevent the flow of gas therethrough when the vent element is wetted by the biological fluid the vent device is also closed, e.g., by capping). Flow control device 27, associated with the conduit 21 between the eluted target cell container 20, and the connector for conduits 11a and 11b, and flow control device 57, associated with conduit 51, are opened. The elution fluid delivery device 50 (e.g., a syringe prefilled with elution solution) is operated, passing elution fluid via the elution fluid inlet port 300, through the porous fibrous leukocyte depletion filter 500 and porous fibrous leukocyte depletion medium 510 via the downstream surface 502 and the upstream surface 501, the inlet port 101a, and into the target cell container 20 via conduits 11b and 21. As the fluid passes through the porous fibrous leukocyte depletion filter 500, target cells are eluted, passing with the elution fluid into the target cell container 20. Flow control devices 27 and 57 are closed. Subsequently, target cell container 20 is disconnected from the system 1500, preferably, while maintaining a closed system.

The collected target cells can be used as desired. For example, the cells can be processed according to one or more of any of the following: seeding in a scaffold or tissue graft, purifying (including removing undesired cells for particular applications, e.g., activated GRAN cells may be removed and/or specific cells may be further isolated), washing, concentrating, freezing (e.g., cryopreserved), and expanding desired cell populations.

The following examples further illustrate the invention but, of course, should not be construed as in any way limiting its scope.

EXAMPLE 1

This example demonstrates leukocytes and stem cells can be recovered from a bone marrow product while reducing red blood cell contamination.

Five units of porcine bone marrow product are each split for processing according to an embodiment of the invention, and a control. The device is configured as generally shown in FIG. 1 and including a diffusing plate having a pattern as shown in FIG. 3A (wherein the perforations each have a diameter of 0.032 inches), and the leukocyte depletion filter is a 3.5 inch disc including a prefilter and 3 layers of melt-blown media prepared as generally described in U.S. Pat. No. 4,925,572. The device is arranged in a system as generally shown in FIG. 8.

The units (100 mL each) are filtered via gravity, and the elution solution (40 mL) comprises saline/10% Dextran-40.

In contrast with the controls, resulting in 89% red blood cell depletion/11% red blood cell contamination/57% white blood cell recovery, the products processed according to an embodiment of the invention resulted in 92% red blood cell depletion/8% red blood cell contamination/52% white blood cell recovery.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A biological fluid filter device comprising:
(a) a housing comprising an inlet port, an upstream chamber, a downstream chamber, and an outlet port and defining a first fluid path between the inlet port and the outlet port, the housing further comprising an elution fluid inlet port and a drain port and defining a second fluid flow path between the elution fluid inlet port and the inlet port;

(b) a porous fibrous leukocyte depletion filter having an upstream surface and a downstream surface, disposed in the housing across the first fluid flow path and across the second fluid path;

(c) a perforated diffusing plate having a first surface and a second surface, disposed in the housing across the first fluid flow path and across the second fluid path, wherein the perforated diffusing plate has asymmetrically shaped perforations through the perforated diffusing plate, the first perforated diffusing plate being disposed between the downstream surface of the porous fibrous leukocyte depletion filter and the outlet port;

wherein the inlet port is upstream of the upstream surface of the porous fibrous leukocyte depletion filter, the outlet port, the elution fluid inlet port, and the drain port, are downstream of the downstream surface of the porous fibrous leukocyte depletion filter and the perforated diffusing plate, and the drain port, in fluid communication with the downstream chamber of the biological fluid filter device, arranged to pass leukocyte-depleted biological fluid from the downstream chamber.

2. The device of claim 1, wherein the housing has a wall downstream of the downstream surface of the porous fibrous leukocyte depletion filter and the perforated diffusing plate, the wall including the elution fluid inlet port, the outlet port, and the drain port, and the elution fluid inlet port is located between the outlet port and the drain port in the wall.

3. The device of claim 2, further comprising a vent device in communication with the outlet port.

4. The device of claim 1, further comprising a vent device in communication with the outlet port.

5. A biological fluid processing system comprising
(a) the biological fluid filter device of claim 1;
(b) a container for receiving leukocyte-depleted biological fluid, in fluid communication with the outlet port;
(c) a container, in fluid communication with the drain port, for receiving gas displaced leukocyte-depleted biological fluid from the drain port; and,
(d) a container for receiving elution fluid and eluted leukocytes, in fluid communication with the inlet port.

6. The system of claim 5, further comprising (e) an elution fluid delivery device, in fluid communication with the elution fluid inlet port.

7. The system of claim 6, wherein the elution fluid delivery device comprises a prefilled syringe containing elution solution or a syringe pump.

8. The system of claim 5, further comprising a biological fluid source container, in fluid communication with the inlet.

9. The system of claim 5, wherein the container for receiving elution fluid and eluted leukocytes is a freezable container.

10. The biological fluid filter device of claim 1, wherein the asymmetrically shaped perforations in the perforated diffusing plate have larger internal diameters at the second surface of the perforated diffusing plate than at the first surface of the perforated diffusing plate, and the first surface of the diffusing plate faces the downstream surface of the porous fibrous leukocyte filter.

11. A method for processing a biological fluid comprising passing the biological fluid through the biological fluid filter device of claim 1.

12. A method for processing a biological fluid comprising
(a) passing the biological fluid from a first container through a biological fluid filter device comprising:
a housing comprising an inlet port, an upstream chamber, a downstream chamber, and an outlet port, and defining a first fluid path between the inlet port and the outlet port, the housing further comprising an elution fluid inlet port and a drain port and defining a second fluid flow path between the elution fluid inlet port and the inlet port, a porous fibrous leukocyte depletion filter having an upstream surface and a downstream surface, disposed in the housing across the first fluid flow path and across the second fluid path; and, a perforated diffusing plate having a first surface and a second surface, disposed in the housing across the first fluid flow path and across the second fluid path, wherein the perforated diffusing plate has asymmetrically shaped perforations through the perforated diffusing plate, the first perforated diffusing plate being disposed between the downstream surface of the porous fibrous leukocyte depletion filter and the outlet port; wherein the inlet port is upstream of the upstream surface of the porous fibrous leukocyte depletion filter, the outlet port, the elution fluid inlet port, and the drain port, are downstream of the downstream surface of the porous fibrous leukocyte depletion filter and the perforated diffusing plate;
and passing leukocyte-depleted biological fluid from the outlet port into a second container;
(b) passing gas through the outlet port and displacing the biological fluid in the downstream chamber from the housing through the drain port into the second container or into a third container; and,
(c) passing elution solution from an elution solution delivery device through the elution fluid inlet port, the perforated diffusing plate, the porous fibrous leukocyte depletion filter, and the inlet port, into an eluted target cell container; wherein the elution solution elutes leukocytes and/or stem cells from the biological fluid filter device into the eluted target cell container.

13. The method of claim 12, comprising passing the gas from the second container through the outlet port and displacing the biological fluid in the downstream chamber from the housing through the drain port into the third container.

14. The method of claim 12, wherein the passing leukocyte-depleted biological fluid from the outlet port includes displacing gas into a gas collection container, and the method further comprises passing collected gas from the gas collection container through the outlet port and displacing addition leukocyte-depleted biological fluid in the downstream chamber from the housing through the drain port into the second container.

15. The method of claim 12, comprising passing the gas through a vent into the outlet port and displacing the biological fluid in the downstream chamber from the housing through the drain port into the second container.

16. The method of claim 12, wherein the asymmetrically shaped perforations in the perforated diffusing plate have larger internal diameters at the second surface of the perforated diffusing plate than at the first surface of the perforated diffusing plate, and the first surface of the diffusing plate faces the downstream surface of the porous fibrous leukocyte filter, and passing elution solution from the elution solution delivery device through the perforated diffusing plate comprises passing the elution solution from the second surface of the diffusing plate through the first surface of the perforated diffusing plate.

17. A method for processing a biological fluid comprising
(a) passing the biological fluid from a first container through a biological fluid filter device comprising:
a housing comprising an inlet port, an upstream chamber, a downstream chamber, and an outlet port, and defining a fluid path between the inlet and the outlet port, the housing further comprising an elution fluid inlet port and a drain port, a porous fibrous leukocyte depletion filter having an upstream surface and a downstream surface, disposed in the housing across the fluid flow path; and, a perforated diffusing plate having a first surface and a second surface, disposed in the housing across the first fluid flow path and across the second fluid path, wherein the perforated diffusing plate has asymmetrically shaped perforations through the perforated diffusing plate, the first perforated diffusing plate being disposed between the downstream surface of the porous fibrous leukocyte depletion filter and the outlet port; wherein the inlet port is upstream of the upstream surface of the porous fibrous leukocyte depletion filter, and the outlet port, the elution fluid inlet port, and the drain port, are downstream of the downstream surface of the porous fibrous leukocyte depletion filter and the perforated diffusing plate;
and passing leukocyte-depleted biological fluid from the outlet port into a second container;
(b) passing gas from the second container through the outlet port and displacing the biological fluid in the downstream chamber from the housing through the drain port into a third container; and,
(c) passing elution solution from an elution solution delivery device through the elution fluid inlet port, the porous fibrous leukocyte depletion filter, and the inlet port, into a fourth container; wherein the elution solution elutes leukocytes and/or stem cells from the biological fluid filter device into the fourth container.

18. The method of claim 17, carried out while maintaining a closed system.

19. The method of claim 17, wherein the asymmetrically shaped perforations in the perforated diffusing plate have larger internal diameters at the second surface of the perforated diffusing plate than at the first surface of the perforated diffusing plate, and the first surface of the diffusing plate faces the downstream surface of the porous fibrous leukocyte filter, and passing elution solution from the elution solution delivery device through the perforated diffusing plate comprises passing the elution solution from the second surface of the diffusing plate through the first surface of the perforated diffusing plate.

* * * * *